US009200304B2

(12) United States Patent
Fukada et al.

(10) Patent No.: US 9,200,304 B2
(45) Date of Patent: *Dec. 1, 2015

(54) METHOD FOR PRODUCING 5'-GUANYLIC ACID

(75) Inventors: Hiroaki Fukada, Kawasaki (JP);
Takayuki Asahara, Kawasaki (JP);
Kenichi Hashiguchi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 364 days.

This patent is subject to a terminal disclaimer.

(21) Appl. No.: 12/851,793

(22) Filed: Aug. 6, 2010

(65) Prior Publication Data

US 2011/0033898 A1    Feb. 10, 2011

(30) Foreign Application Priority Data

Aug. 10, 2009 (JP) ................ 2009-185920

(51) Int. Cl.
| | | |
|---|---|---|
| C12P 19/38 | (2006.01) | |
| C12N 1/00 | (2006.01) | |
| C12N 1/20 | (2006.01) | |
| C07H 21/04 | (2006.01) | |
| C12P 19/32 | (2006.01) | |
| C12N 9/04 | (2006.01) | |

(52) U.S. Cl.
CPC ............... *C12P 19/32* (2013.01); *C12N 9/0006* (2013.01)

(58) Field of Classification Search
None
See application file for complete search history.

(56) References Cited

U.S. PATENT DOCUMENTS

| | | | |
|---|---|---|---|
| 7,211,416 B2 | 5/2007 | Asahara et al. | |
| 7,326,546 B2 | 2/2008 | Matsuno et al. | |
| 8,309,329 B2 * | 11/2012 | Asahara et al. | 435/87 |
| 2002/0098494 A1 | 7/2002 | Kakehi et al. | |
| 2008/0299620 A1 * | 12/2008 | Park et al. | 435/89 |
| 2008/0318278 A1 | 12/2008 | Pan et al. | |
| 2009/0104665 A1 | 4/2009 | Asahara et al. | |
| 2009/0186384 A1 | 7/2009 | Matsuno et al. | |
| 2010/0047874 A1 | 2/2010 | Asahara et al. | |
| 2011/0045543 A1 * | 2/2011 | Asahara et al. | 435/92 |

FOREIGN PATENT DOCUMENTS

| | | | |
|---|---|---|---|
| CN | 1335403 | | 2/2002 |
| EP | 0263716 | * | 4/1988 |
| JP | 56-12438 | | 3/1981 |
| JP | 07-231793 | | 9/1995 |
| JP | 10-201481 | | 8/1998 |
| JP | 2001-245676 | | 9/2001 |
| JP | 2002-355087 | | 12/2002 |
| WO | WO96/37603 | | 11/1996 |
| WO | WO2006/078132 | | 7/2006 |
| WO | WO2007/069861 | | 6/2007 |
| WO | WO 2009/107631 A1 | * | 9/2009 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Fujio, T., et al., "High Level Expression of XMP Aminase in *Escherichia coli* and Its Application for the Industrial Production of 5'-Guanylic Acid," Biosci. Biotech. Biochem. 1997;61(5):840-845.
Kuznetsova, E., et al., "Genome-wide Analysis of Substrate Specificities of the *Escherichia coli* Haloacid Dehalogenase-like Phosphatase Family," J. Biol. Chem. 2006;281(47):36149-36161.
Peri, K. G., et al., "Cloning and characterization of the N-acetylglucosamine operon of *Escherichia coli*," Biochem. Cell Biol. 1990;68:123-137.
Plumbridge, J. A., "Sequence of the nagBACD operon in *Escherichia coli* K12 and pattern of transcription within the nag regulon," Mol. Microbiol. 1989;3(4):505-515.
Tremblay, L. W., et al., "Structure and Activity Analyses of *Escherichia coli* K-12 NagD Provide Insight into the Evolution of Biochemical Function in the Haloalkanoic Acid Dehalogenase Superfamily," Biochem. 2006;45:1183-1193.
Extended European Search Report for EP Patent App. No. EP10008338 (Oct. 8, 2012).
Swiss-Prot, P04079, A.A. Tiedeman et al., pp. 1-23, the amino acid sequence; Last modified Jul. 24, 2013, version 140.
Office Action from Chinese Patent App. No. 201010250541.1 (Jul. 24, 2013).

* cited by examiner

*Primary Examiner* — Iqbal H Chowdhury
(74) *Attorney, Agent, or Firm* — Shelly Guest Cermak; Cermak Nakajima & McGowan LLP

(57) ABSTRACT

5'-guanylic acid (GMP) is produced efficiently by allowing a microorganism to react with xanthylic acid (XMP), wherein said microorganism is able to convert xanthylic acid into 5'-guanylic acid and has been modified so that the nagD gene does not function normally and 5'-guanylic acid synthetase activity is enhanced.

15 Claims, 1 Drawing Sheet

(A)

(B)

(A)

(B)

(A)

(B)

```
                        SEQUENCE LISTING

<160> NUMBER OF SEQ ID NOS: 24

<210> SEQ ID NO 1
<211> LENGTH: 1578
<212> TYPE: DNA
<213> ORGANISM: Escherichia coli
<220> FEATURE:
<221> NAME/KEY: CDS
<222> LOCATION: (1)..(1575)

<400> SEQUENCE: 1 atg acg gaa aac att cat aag cat cgc atc ctc att ctg gac ttc ggt        48
Met Thr Glu Asn Ile His Lys His Arg Ile Leu Ile Leu Asp Phe Gly
1               5                   10                  15 tct cag tac act caa ctg gtt gcg cgc cgc gtg cgt gag ctg ggt gtt        96
Ser Gln Tyr Thr Gln Leu Val Ala Arg Arg Val Arg Glu Leu Gly Val
            20                  25                  30 tac tgc gaa ctg tgg gcg tgg gat gtg aca gaa gca caa att cgt gac       144
Tyr Cys Glu Leu Trp Ala Trp Asp Val Thr Glu Ala Gln Ile Arg Asp
        35                  40                  45 ttc aat cca agc ggc att att ctt tcc ggc ggc ccg gaa agt act act       192
Phe Asn Pro Ser Gly Ile Ile Leu Ser Gly Gly Pro Glu Ser Thr Thr
    50                  55                  60 gaa gaa aac agt ccg cgt gcg ccg cag tat gtc ttt gaa gca ggc gta       240
Glu Glu Asn Ser Pro Arg Ala Pro Gln Tyr Val Phe Glu Ala Gly Val
65                  70                  75                  80 ccg gta ttc ggc gtt tgc tat ggc atg cag acc atg gca atg cag ttg       288
Pro Val Phe Gly Val Cys Tyr Gly Met Gln Thr Met Ala Met Gln Leu
                85                  90                  95 ggc ggt cac gtt gaa gcc tct aac gaa cgt gaa ttt ggc tac gcg cag       336
Gly Gly His Val Glu Ala Ser Asn Glu Arg Glu Phe Gly Tyr Ala Gln
            100                 105                 110 gtt gaa gtc gta aac gac agc gca ctg gtt cgc ggt atc gaa gat gcg       384
Val Glu Val Val Asn Asp Ser Ala Leu Val Arg Gly Ile Glu Asp Ala
        115                 120                 125 ctg acc gca gac ggt aaa ccg ctc ctc gat gtc tgg atg agc cac ggc       432
Leu Thr Ala Asp Gly Lys Pro Leu Leu Asp Val Trp Met Ser His Gly
    130                 135                 140 gat aaa gtt acc gct att ccg tcc gac ttc atc acc gta gcc agc acc       480
Asp Lys Val Thr Ala Ile Pro Ser Asp Phe Ile Thr Val Ala Ser Thr
145                 150                 155                 160
```

-continued

```
gaa agc tgc ccg ttt gcc att atg gct aac gaa gaa aaa cgc ttc tat      528
Glu Ser Cys Pro Phe Ala Ile Met Ala Asn Glu Glu Lys Arg Phe Tyr
            165                 170                 175 ggc gta cag ttc cac ccg gaa gtg act cat acc cgc cag ggt atg cgc      576
Gly Val Gln Phe His Pro Glu Val Thr His Thr Arg Gln Gly Met Arg
        180                 185                 190 atg ctg gag cgt ttt gtg cgt gat atc tgc cag tgt gaa gcc ctg tgg      624
Met Leu Glu Arg Phe Val Arg Asp Ile Cys Gln Cys Glu Ala Leu Trp
    195                 200                 205 acg cca gcg aaa att atc gac gat gct gta gct cgc atc cgc gag cag      672
Thr Pro Ala Lys Ile Ile Asp Asp Ala Val Ala Arg Ile Arg Glu Gln
210                 215                 220 gta ggc gac gat aaa gtc atc ctc ggc ctc tct ggt ggt gtg gat tcc      720
Val Gly Asp Asp Lys Val Ile Leu Gly Leu Ser Gly Gly Val Asp Ser
225                 230                 235                 240 tcc gta acc gca atg ctg ctc cac cgc gct atc ggt aaa aac ctg act      768
Ser Val Thr Ala Met Leu Leu His Arg Ala Ile Gly Lys Asn Leu Thr
                245                 250                 255 tgc gta ttc gtc gac aac ggc ctg ctg cgc ctc aac gaa gca gag cag      816
Cys Val Phe Val Asp Asn Gly Leu Leu Arg Leu Asn Glu Ala Glu Gln
            260                 265                 270 gtt ctg gat atg ttt ggc gat cac ttt ggt ctt aac att gtt cac gta      864
Val Leu Asp Met Phe Gly Asp His Phe Gly Leu Asn Ile Val His Val
        275                 280                 285 ccg gca gaa gat cgc ttc ctg tca gcg ctg gct ggc gaa aac gat ccg      912
Pro Ala Glu Asp Arg Phe Leu Ser Ala Leu Ala Gly Glu Asn Asp Pro
    290                 295                 300 gaa gca aaa cgt aaa atc atc ggt cgc gtt ttc gtt gaa gta ttc gat      960
Glu Ala Lys Arg Lys Ile Ile Gly Arg Val Phe Val Glu Val Phe Asp
305                 310                 315                 320 gaa gaa gcg ctg aaa ctg gaa gac gtg aag tgg ctg gcg cag ggc acc     1008
Glu Glu Ala Leu Lys Leu Glu Asp Val Lys Trp Leu Ala Gln Gly Thr
                325                 330                 335 atc tac cct gac gtt atc gaa tct gcg gcg tct gca acc ggt aaa gca     1056
Ile Tyr Pro Asp Val Ile Glu Ser Ala Ala Ser Ala Thr Gly Lys Ala
            340                 345                 350 cac gtc atc aaa tct cac cac aac gtg ggc ggc ctg ccg aaa gag atg     1104
His Val Ile Lys Ser His His Asn Val Gly Gly Leu Pro Lys Glu Met
        355                 360                 365 aag atg ggc ctg gtt gaa ccg ctg aaa gag ctg ttc aaa gac gaa gtg     1152
Lys Met Gly Leu Val Glu Pro Leu Lys Glu Leu Phe Lys Asp Glu Val
    370                 375                 380 cgt aag att ggt ctg gag ctg ggc ctg ccg tac gac atg ctg tac cgt     1200
Arg Lys Ile Gly Leu Glu Leu Gly Leu Pro Tyr Asp Met Leu Tyr Arg
385                 390                 395                 400 cac ccg ttc ccg gga cca ggc ctt ggc gtt cgt gtt ctg ggt gaa gtg     1248
His Pro Phe Pro Gly Pro Gly Leu Gly Val Arg Val Leu Gly Glu Val
                405                 410                 415 aag aaa gag tac tgt gac ctg ctg cgc cgt gct gac gcc atc ttc att     1296
Lys Lys Glu Tyr Cys Asp Leu Leu Arg Arg Ala Asp Ala Ile Phe Ile
            420                 425                 430 gaa gaa ctg cgt aaa gcg gac ctg tac gac aaa gtc agc cag gcg ttc     1344
Glu Glu Leu Arg Lys Ala Asp Leu Tyr Asp Lys Val Ser Gln Ala Phe
        435                 440                 445 act gtg ttc ctg ccg gta cgt tcc gtt ggc gta atg ggc gat ggt cgt     1392
Thr Val Phe Leu Pro Val Arg Ser Val Gly Val Met Gly Asp Gly Arg
    450                 455                 460 aag tat gac tgg gtt gtc tct ctg cgt gct gtc gaa acc atc gac ttt     1440
Lys Tyr Asp Trp Val Val Ser Leu Arg Ala Val Glu Thr Ile Asp Phe
```

```
                465                 470                 475                 480
atg acc gca cac tgg gcg cat ctg ccg tac gat ttc ctc ggt cgc gtt           1488
Met Thr Ala His Trp Ala His Leu Pro Tyr Asp Phe Leu Gly Arg Val
                    485                 490                 495 tcc aac cgc att atc aat gaa gtg aac ggt att tcc cgc gtg gtg tat           1536
Ser Asn Arg Ile Ile Asn Glu Val Asn Gly Ile Ser Arg Val Val Tyr
                500                 505                 510 gac atc agc ggc aag ccg cca gct acc att gag tgg gaa tga               1578
Asp Ile Ser Gly Lys Pro Pro Ala Thr Ile Glu Trp Glu
                515                 520                 525
```

<210> SEQ ID NO 2
<211> LENGTH: 525
<212> TYPE: PRT
<213> ORGANISM: Escherichia coli

<400> SEQUENCE: 2

```
Met Thr Glu Asn Ile His Lys His Arg Ile Leu Ile Leu Asp Phe Gly
1               5                   10                  15

Ser Gln Tyr Thr Gln Leu Val Ala Arg Val Arg Glu Leu Gly Val
                20                  25                  30

Tyr Cys Glu Leu Trp Ala Trp Asp Val Thr Glu Ala Gln Ile Arg Asp
            35                  40                  45

Phe Asn Pro Ser Gly Ile Ile Leu Ser Gly Gly Pro Glu Ser Thr Thr
        50                  55                  60

Glu Glu Asn Ser Pro Arg Ala Pro Gln Tyr Val Phe Glu Ala Gly Val
65                  70                  75                  80

Pro Val Phe Gly Val Cys Tyr Gly Met Gln Thr Met Ala Met Gln Leu
                85                  90                  95

Gly Gly His Val Glu Ala Ser Asn Glu Arg Glu Phe Gly Tyr Ala Gln
            100                 105                 110

Val Glu Val Val Asn Asp Ser Ala Leu Val Arg Gly Ile Glu Asp Ala
        115                 120                 125

Leu Thr Ala Asp Gly Lys Pro Leu Leu Asp Val Trp Met Ser His Gly
130                 135                 140

Asp Lys Val Thr Ala Ile Pro Ser Asp Phe Ile Thr Val Ala Ser Thr
145                 150                 155                 160

Glu Ser Cys Pro Phe Ala Ile Met Ala Asn Glu Glu Lys Arg Phe Tyr
                165                 170                 175

Gly Val Gln Phe His Pro Glu Val Thr His Thr Arg Gln Gly Met Arg
            180                 185                 190

Met Leu Glu Arg Phe Val Arg Asp Ile Cys Gln Cys Glu Ala Leu Trp
        195                 200                 205

Thr Pro Ala Lys Ile Ile Asp Asp Ala Val Ala Arg Ile Arg Glu Gln
210                 215                 220

Val Gly Asp Lys Val Ile Leu Gly Leu Ser Gly Gly Val Asp Ser
225                 230                 235                 240

Ser Val Thr Ala Met Leu Leu His Arg Ala Ile Gly Lys Asn Leu Thr
                245                 250                 255

Cys Val Phe Val Asp Asn Gly Leu Leu Arg Leu Asn Glu Ala Glu Gln
            260                 265                 270

Val Leu Asp Met Phe Gly Asp His Phe Gly Leu Asn Ile Val His Val
        275                 280                 285

Pro Ala Glu Asp Arg Phe Leu Ser Ala Leu Ala Gly Glu Asn Asp Pro
290                 295                 300
```

```
Glu Ala Lys Arg Lys Ile Ile Gly Arg Val Phe Val Glu Val Phe Asp
305                 310                 315                 320

Glu Glu Ala Leu Lys Leu Glu Asp Val Lys Trp Leu Ala Gln Gly Thr
            325                 330                 335

Ile Tyr Pro Asp Val Ile Glu Ser Ala Ala Ser Ala Thr Gly Lys Ala
                340                 345                 350

His Val Ile Lys Ser His His Asn Val Gly Gly Leu Pro Lys Glu Met
            355                 360                 365

Lys Met Gly Leu Val Glu Pro Leu Lys Glu Leu Phe Lys Asp Glu Val
    370                 375                 380

Arg Lys Ile Gly Leu Glu Leu Gly Leu Pro Tyr Asp Met Leu Tyr Arg
385                 390                 395                 400

His Pro Phe Pro Gly Pro Gly Leu Gly Val Arg Val Leu Gly Glu Val
                405                 410                 415

Lys Lys Glu Tyr Cys Asp Leu Leu Arg Arg Ala Asp Ala Ile Phe Ile
            420                 425                 430

Glu Glu Leu Arg Lys Ala Asp Leu Tyr Asp Lys Val Ser Gln Ala Phe
            435                 440                 445

Thr Val Phe Leu Pro Val Arg Ser Val Gly Val Met Gly Asp Gly Arg
450                 455                 460

Lys Tyr Asp Trp Val Val Ser Leu Arg Ala Val Glu Thr Ile Asp Phe
465                 470                 475                 480

Met Thr Ala His Trp Ala His Leu Pro Tyr Asp Phe Leu Gly Arg Val
                485                 490                 495

Ser Asn Arg Ile Ile Asn Glu Val Asn Gly Ile Ser Arg Val Val Tyr
            500                 505                 510

Asp Ile Ser Gly Lys Pro Pro Ala Thr Ile Glu Trp Glu
            515                 520                 525

<210> SEQ ID NO 3
<211> LENGTH: 1542
<212> TYPE: DNA
<213> ORGANISM: Bacillus subtilis
<220> FEATURE:
<221> NAME/KEY: CDS
<222> LOCATION: (1)..(1539)

<400> SEQUENCE: 3 atg aca aag tta gtg aat gaa atg att ctt gtc ctt gat ttc ggc agt    48
Met Thr Lys Leu Val Asn Glu Met Ile Leu Val Leu Asp Phe Gly Ser
1               5                   10                  15 cag tat aac cag ctg att aca cgc cgt atc cgt gaa ttc ggt gtt tac    96
Gln Tyr Asn Gln Leu Ile Thr Arg Arg Ile Arg Glu Phe Gly Val Tyr
            20                  25                  30 agc gag ctg cat cca cat aca ttg acg gct gaa gaa att aaa aaa atg   144
Ser Glu Leu His Pro His Thr Leu Thr Ala Glu Glu Ile Lys Lys Met
        35                  40                  45 aat cca aaa gga att att tta tcc ggc ggt cca aac agt gtg tat gat   192
Asn Pro Lys Gly Ile Ile Leu Ser Gly Gly Pro Asn Ser Val Tyr Asp
50                  55                  60 gaa aac tct ttc cgc tgt gac gag aaa atc ttc gag ctt gat att cct   240
Glu Asn Ser Phe Arg Cys Asp Glu Lys Ile Phe Glu Leu Asp Ile Pro
65                  70                  75                  80 gtt ttg gga att tgc tac ggc atg cag ctg atg act cat tac ctt ggc   288
Val Leu Gly Ile Cys Tyr Gly Met Gln Leu Met Thr His Tyr Leu Gly
                85                  90                  95 ggt aaa gtt gaa gcg gca agc cag cgt gaa tac gga aaa gca aac atc   336
Gly Lys Val Glu Ala Ala Ser Gln Arg Glu Tyr Gly Lys Ala Asn Ile
```

-continued

```
              100                 105                 110
cgc atc gaa ggc aca cct gat ttg ttc aga gat ctt ccg aat gaa caa    384
Arg Ile Glu Gly Thr Pro Asp Leu Phe Arg Asp Leu Pro Asn Glu Gln
            115                 120                 125 gtg gtt tgg atg agc cac ggc gat ttg gtt gta gaa gtt cct gaa ggc    432
Val Val Trp Met Ser His Gly Asp Leu Val Val Glu Val Pro Glu Gly
        130                 135                 140 ttc act gtt gac gcg aca agc cat cac tgc ccg aac tca gca atg agc    480
Phe Thr Val Asp Ala Thr Ser His His Cys Pro Asn Ser Ala Met Ser
145                 150                 155                 160 aaa gcg gac aaa aaa tgg tat ggc gtt cag ttc cac ccg gaa gtg cgc    528
Lys Ala Asp Lys Lys Trp Tyr Gly Val Gln Phe His Pro Glu Val Arg
                165                 170                 175 cac tct gaa tac ggc aat gat ctt ctg aaa aac ttt gta ttc ggt gtt    576
His Ser Glu Tyr Gly Asn Asp Leu Leu Lys Asn Phe Val Phe Gly Val
            180                 185                 190 tgc gaa tgc gaa ggc gaa tgg tca atg gag aac ttt atc gaa atc gaa    624
Cys Glu Cys Glu Gly Glu Trp Ser Met Glu Asn Phe Ile Glu Ile Glu
        195                 200                 205 atg caa aaa atc cgt gaa acg gtc gga gac aaa cag gtt ctt tgc gcg    672
Met Gln Lys Ile Arg Glu Thr Val Gly Asp Lys Gln Val Leu Cys Ala
210                 215                 220 cta agc ggc ggc gtt gat tcc tct gtt gtt gct gtt ttg att cat aaa    720
Leu Ser Gly Gly Val Asp Ser Ser Val Val Ala Val Leu Ile His Lys
225                 230                 235                 240 gcg atc ggc gac cag ctg act tgt atc ttt gta gac cat ggt ctt ctc    768
Ala Ile Gly Asp Gln Leu Thr Cys Ile Phe Val Asp His Gly Leu Leu
                245                 250                 255 cgt aaa ggc gaa gct gag ggt gtt atg aaa aca ttc agc gaa ggc ttt    816
Arg Lys Gly Glu Ala Glu Gly Val Met Lys Thr Phe Ser Glu Gly Phe
            260                 265                 270 aac atg aat gtg att aaa gta gac gca aaa gat cga ttc tta aac aaa    864
Asn Met Asn Val Ile Lys Val Asp Ala Lys Asp Arg Phe Leu Asn Lys
        275                 280                 285 cta aaa ggc gtt tct gat cct gag caa aaa cgc aaa atc atc ggt aat    912
Leu Lys Gly Val Ser Asp Pro Glu Gln Lys Arg Lys Ile Ile Gly Asn
290                 295                 300 gaa ttc att tac gtg ttt gat gat gaa gcg gac aag ctc aaa ggc atc    960
Glu Phe Ile Tyr Val Phe Asp Asp Glu Ala Asp Lys Leu Lys Gly Ile
305                 310                 315                 320 gac tac ctt gca caa ggt acg ctt tac aca gat atc atc gag agc ggt   1008
Asp Tyr Leu Ala Gln Gly Thr Leu Tyr Thr Asp Ile Ile Glu Ser Gly
                325                 330                 335 aca gca acg gcg caa acg atc aaa tct cac cac aat gtc ggc gga ctt   1056
Thr Ala Thr Ala Gln Thr Ile Lys Ser His His Asn Val Gly Gly Leu
            340                 345                 350 cct gaa gac atg cag ttt gag ctg atc gag ccg tta aat acg ctc ttc   1104
Pro Glu Asp Met Gln Phe Glu Leu Ile Glu Pro Leu Asn Thr Leu Phe
        355                 360                 365 aaa gac gaa gtg cgc gcg ctt ggc aca gag ctc ggc att ccg gat gaa   1152
Lys Asp Glu Val Arg Ala Leu Gly Thr Glu Leu Gly Ile Pro Asp Glu
370                 375                 380 atc gta tgg cgt cag ccg ttc cca gga ccg gga ctc gga atc cgc gtt   1200
Ile Val Trp Arg Gln Pro Phe Pro Gly Pro Gly Leu Gly Ile Arg Val
385                 390                 395                 400 ctt ggc gaa gta aca gaa gaa aaa ctt gaa atc gtt cgt gaa tca gat   1248
Leu Gly Glu Val Thr Glu Glu Lys Leu Glu Ile Val Arg Glu Ser Asp
                405                 410                 415 gca atc ttg cgt gaa gaa att gca aat cac ggc tta gag cgt gat atc   1296
```

-continued

```
Ala Ile Leu Arg Glu Glu Ile Ala Asn His Gly Leu Glu Arg Asp Ile
            420                 425                 430 tgg caa tac ttc act gtt ctt cct gac atc cgc agc gtt ggt gtt atg      1344
Trp Gln Tyr Phe Thr Val Leu Pro Asp Ile Arg Ser Val Gly Val Met
            435                 440                 445 ggt gac gca aga aca tat gat tac aca atc gga atc cgc gcc gtt aca      1392
Gly Asp Ala Arg Thr Tyr Asp Tyr Thr Ile Gly Ile Arg Ala Val Thr
        450                 455                 460 tca atc gac ggc atg aca tct gac tgg gcg cgt atc ccg tgg gat gtg      1440
Ser Ile Asp Gly Met Thr Ser Asp Trp Ala Arg Ile Pro Trp Asp Val
465                 470                 475                 480 ctt gaa gtc att tcg aca cgt atc gta aac gaa gtg aag cac att aac      1488
Leu Glu Val Ile Ser Thr Arg Ile Val Asn Glu Val Lys His Ile Asn
                485                 490                 495 cgc gtg gtg tat gat att aca agt aag ccg cct gcg acg att gag tgg      1536
Arg Val Val Tyr Asp Ile Thr Ser Lys Pro Pro Ala Thr Ile Glu Trp
            500                 505                 510 gaa taa                                                              1542
Glu
```

<210> SEQ ID NO 4
<211> LENGTH: 513
<212> TYPE: PRT
<213> ORGANISM: Bacillus subtilis

<400> SEQUENCE: 4

```
Met Thr Lys Leu Val Asn Glu Met Ile Leu Val Leu Asp Phe Gly Ser
1               5                   10                  15

Gln Tyr Asn Gln Leu Ile Thr Arg Arg Ile Arg Glu Phe Gly Val Tyr
            20                  25                  30

Ser Glu Leu His Pro His Thr Leu Thr Ala Glu Glu Ile Lys Lys Met
        35                  40                  45

Asn Pro Lys Gly Ile Ile Leu Ser Gly Gly Pro Asn Ser Val Tyr Asp
    50                  55                  60

Glu Asn Ser Phe Arg Cys Asp Glu Lys Ile Phe Glu Leu Asp Ile Pro
65                  70                  75                  80

Val Leu Gly Ile Cys Tyr Gly Met Gln Leu Met Thr His Tyr Leu Gly
                85                  90                  95

Gly Lys Val Glu Ala Ala Ser Gln Arg Glu Tyr Gly Lys Ala Asn Ile
            100                 105                 110

Arg Ile Glu Gly Thr Pro Asp Leu Phe Arg Asp Leu Pro Asn Glu Gln
        115                 120                 125

Val Val Trp Met Ser His Gly Asp Leu Val Val Glu Val Pro Glu Gly
    130                 135                 140

Phe Thr Val Asp Ala Thr Ser His His Cys Pro Asn Ser Ala Met Ser
145                 150                 155                 160

Lys Ala Asp Lys Lys Trp Tyr Gly Val Gln Phe His Pro Glu Val Arg
                165                 170                 175

His Ser Glu Tyr Gly Asn Asp Leu Leu Lys Asn Phe Val Phe Gly Val
            180                 185                 190

Cys Glu Cys Glu Gly Glu Trp Ser Met Glu Asn Phe Ile Glu Ile
        195                 200                 205

Met Gln Lys Ile Arg Glu Thr Val Gly Asp Lys Gln Val Leu Cys Ala
    210                 215                 220

Leu Ser Gly Gly Val Asp Ser Ser Val Val Ala Val Leu Ile His Lys
225                 230                 235                 240
```

```
Ala Ile Gly Asp Gln Leu Thr Cys Ile Phe Val Asp His Gly Leu Leu
            245                 250                 255

Arg Lys Gly Glu Ala Glu Gly Val Met Lys Thr Phe Ser Glu Gly Phe
        260                 265                 270

Asn Met Asn Val Ile Lys Val Asp Ala Lys Asp Arg Phe Leu Asn Lys
            275                 280                 285

Leu Lys Gly Val Ser Asp Pro Glu Gln Lys Arg Lys Ile Ile Gly Asn
        290                 295                 300

Glu Phe Ile Tyr Val Phe Asp Asp Glu Ala Asp Lys Leu Lys Gly Ile
305                 310                 315                 320

Asp Tyr Leu Ala Gln Gly Thr Leu Tyr Thr Asp Ile Ile Glu Ser Gly
                325                 330                 335

Thr Ala Thr Ala Gln Thr Ile Lys Ser His His Asn Val Gly Gly Leu
            340                 345                 350

Pro Glu Asp Met Gln Phe Glu Leu Ile Glu Pro Leu Asn Thr Leu Phe
        355                 360                 365

Lys Asp Glu Val Arg Ala Leu Gly Thr Glu Leu Gly Ile Pro Asp Glu
    370                 375                 380

Ile Val Trp Arg Gln Pro Phe Pro Gly Pro Gly Leu Gly Ile Arg Val
385                 390                 395                 400

Leu Gly Glu Val Thr Glu Glu Lys Leu Glu Ile Val Arg Glu Ser Asp
                405                 410                 415

Ala Ile Leu Arg Glu Glu Ile Ala Asn His Gly Leu Glu Arg Asp Ile
            420                 425                 430

Trp Gln Tyr Phe Thr Val Leu Pro Asp Ile Arg Ser Val Gly Val Met
        435                 440                 445

Gly Asp Ala Arg Thr Tyr Asp Tyr Thr Ile Gly Ile Arg Ala Val Thr
    450                 455                 460

Ser Ile Asp Gly Met Thr Ser Asp Trp Ala Arg Ile Pro Trp Asp Val
465                 470                 475                 480

Leu Glu Val Ile Ser Thr Arg Ile Val Asn Glu Val Lys His Ile Asn
                485                 490                 495

Arg Val Val Tyr Asp Ile Thr Ser Lys Pro Pro Ala Thr Ile Glu Trp
            500                 505                 510

Glu

<210> SEQ ID NO 5
<211> LENGTH: 1572
<212> TYPE: DNA
<213> ORGANISM: Corynebacterium glutamicum
<220> FEATURE:
<221> NAME/KEY: CDS
<222> LOCATION: (1)..(1569)

<400> SEQUENCE: 5 gtg agc ctt cag aca aat cat cgc cca gta ctc gtc gtt gac ttc ggc      48
Val Ser Leu Gln Thr Asn His Arg Pro Val Leu Val Val Asp Phe Gly
1               5                   10                  15 gca cag tac gcg cag ctg atc gca cgt cgt gtg cgt gag gcc ggc atc      96
Ala Gln Tyr Ala Gln Leu Ile Ala Arg Arg Val Arg Glu Ala Gly Ile
                20                  25                  30 tac tcc gaa gtc atc ccg cac acc gcc acc gca gac gat gtg cgc gct    144
Tyr Ser Glu Val Ile Pro His Thr Ala Thr Ala Asp Asp Val Arg Ala
            35                  40                  45 aaa aat gca gca gcc ctc gtc ctt tcc ggt ggc cca tcc tcc gtg tat    192
Lys Asn Ala Ala Ala Leu Val Leu Ser Gly Gly Pro Ser Ser Val Tyr
        50                  55                  60
```

-continued

| | | |
|---|---|---|
| gcc gag gga gca cca tcc ctt gac gct gag att ctt gat ctc gga ttg<br>Ala Glu Gly Ala Pro Ser Leu Asp Ala Glu Ile Leu Asp Leu Gly Leu<br>65                    70                   75               80 | 240 |
| cca gta ttt ggc att tgc tac ggc ttc caa gcc atg acc cac gcg ctt<br>Pro Val Phe Gly Ile Cys Tyr Gly Phe Gln Ala Met Thr His Ala Leu<br>                   85                   90                   95 | 288 |
| ggt ggc acc gtt gcc aac acc ggt aag cgc gaa tac gga cgc acc gac<br>Gly Gly Thr Val Ala Asn Thr Gly Lys Arg Glu Tyr Gly Arg Thr Asp<br>                  100                    105                   110 | 336 |
| atc aac gtt gcc ggt ggc gtc ctc cac gaa ggc ctc gaa gcc tgc cac<br>Ile Asn Val Ala Gly Gly Val Leu His Glu Gly Leu Glu Ala Cys His<br>                  115                    120                   125 | 384 |
| aag gtg tgg atg agc cac ggc gac gcc gtc tct gaa gcc cca gaa ggt<br>Lys Val Trp Met Ser His Gly Asp Ala Val Ser Glu Ala Pro Glu Gly<br>130                    135                   140 | 432 |
| ttc gta gtc acc gcg tcc tcc gaa ggt gcg cct gtc gca gct ttc gaa<br>Phe Val Val Thr Ala Ser Ser Glu Gly Ala Pro Val Ala Ala Phe Glu<br>145                    150                   155                   160 | 480 |
| aac aag gaa cgc aaa atg gct ggc gtg cag tac cac cca gag gta ttg<br>Asn Lys Glu Arg Lys Met Ala Gly Val Gln Tyr His Pro Glu Val Leu<br>                  165                    170                   175 | 528 |
| cac tca cca cac ggc cag gca gtt ctg acc cgc ttc ctc act gag atc<br>His Ser Pro His Gly Gln Ala Val Leu Thr Arg Phe Leu Thr Glu Ile<br>                  180                    185                   190 | 576 |
| gca ggt cta gag cag aac tgg acc gca gca aac atc gct gaa gaa ctc<br>Ala Gly Leu Glu Gln Asn Trp Thr Ala Ala Asn Ile Ala Glu Glu Leu<br>               195                    200                   205 | 624 |
| atc gaa aag gtc cgc gag cag atc ggc gaa gat ggc cgc gct att tgt<br>Ile Glu Lys Val Arg Glu Gln Ile Gly Glu Asp Gly Arg Ala Ile Cys<br>210                    215                    220 | 672 |
| ggc cta tcc ggt ggt gtg gac tcc gct gtt gcc ggt gct ttg gtg cag<br>Gly Leu Ser Gly Gly Val Asp Ser Ala Val Ala Gly Ala Leu Val Gln<br>225                    230                   235                  240 | 720 |
| cgc gcc att ggt gac cgt ttg acc tgt gtc ttt gtt gac cac ggt ctg<br>Arg Ala Ile Gly Asp Arg Leu Thr Cys Val Phe Val Asp His Gly Leu<br>                       245                    250                   255 | 768 |
| ctg cgt gcc ggt gag cgc gag cag gtg gaa aaa gac ttc gtc gca gca<br>Leu Arg Ala Gly Glu Arg Glu Gln Val Glu Lys Asp Phe Val Ala Ala<br>               260                    265                   270 | 816 |
| acc ggc gcc aag ctg gtt acc gtt gat gag cgc cag gca ttc cta tcc<br>Thr Gly Ala Lys Leu Val Thr Val Asp Glu Arg Gln Ala Phe Leu Ser<br>             275                    280                   285 | 864 |
| aag ctg gcc gga gtt acc gaa cca gaa gca aag cgc aag gct atc ggc<br>Lys Leu Ala Gly Val Thr Glu Pro Glu Ala Lys Arg Lys Ala Ile Gly<br>290                    295                    300 | 912 |
| gct gag ttc atc cgc tcc ttc gag cgc gca gtt gcc ggt gtg ctg gaa<br>Ala Glu Phe Ile Arg Ser Phe Glu Arg Ala Val Ala Gly Val Leu Glu<br>305                    310                    315                   320 | 960 |
| gaa gct cca gaa ggt tcc acc gtg gac ttc ctg gtt cag ggc acc ctg<br>Glu Ala Pro Glu Gly Ser Thr Val Asp Phe Leu Val Gln Gly Thr Leu<br>                       325                    330                   335 | 1008 |
| tac cca gac gtc gtg gaa tcc ggt ggt gga tct ggt acc gca aac atc<br>Tyr Pro Asp Val Val Glu Ser Gly Gly Gly Ser Gly Thr Ala Asn Ile<br>                  340                    345                   350 | 1056 |
| aag agc cac cac aac gtc ggt gga ctg cca gac gat gtg gaa ttc aag<br>Lys Ser His His Asn Val Gly Gly Leu Pro Asp Asp Val Glu Phe Lys<br>               355                    360                   365 | 1104 |
| ctt gtt gag cca ctg cgt gac ctc ttc aaa gac gaa gtc cgt gcc gtt<br>Leu Val Glu Pro Leu Arg Asp Leu Phe Lys Asp Glu Val Arg Ala Val | 1152 |

```
                370             375             380
ggc cgt gaa ctt ggc ctg cct gag gaa atc gtt ggc cgc cag cca ttc      1200
Gly Arg Glu Leu Gly Leu Pro Glu Glu Ile Val Gly Arg Gln Pro Phe
385                 390                 395                 400 cca gga cca gga ctt ggt atc cgc atc atc ggt gaa gtc acc gaa gat      1248
Pro Gly Pro Gly Leu Gly Ile Arg Ile Ile Gly Glu Val Thr Glu Asp
            405                 410                 415 cgc cta gaa acc ctc cgc cac gct gac ctg atc gcc cgc acc gag ctc      1296
Arg Leu Glu Thr Leu Arg His Ala Asp Leu Ile Ala Arg Thr Glu Leu
        420                 425                 430 acc gaa gcc gga ctt gac ggc gtg atc tgg cag tgc cca gta gtc ctc      1344
Thr Glu Ala Gly Leu Asp Gly Val Ile Trp Gln Cys Pro Val Val Leu
    435                 440                 445 ctg gca gat gtc cgc tct gtt ggt gtt caa ggc gat ggc cgc acc tac      1392
Leu Ala Asp Val Arg Ser Val Gly Val Gln Gly Asp Gly Arg Thr Tyr
450                 455                 460 gga cac cca atc gtg ctg cgc cca gtg tct tcc gaa gac gca atg acc      1440
Gly His Pro Ile Val Leu Arg Pro Val Ser Ser Glu Asp Ala Met Thr
465                 470                 475                 480 gcc gac tgg acc cgc ctg cca tac gag gtt ctg gag aag atc tcc acc      1488
Ala Asp Trp Thr Arg Leu Pro Tyr Glu Val Leu Glu Lys Ile Ser Thr
            485                 490                 495 cgc atc acc aac gaa gtt cca gat gtg aac cgc gtg gtg ctg gac gta      1536
Arg Ile Thr Asn Glu Val Pro Asp Val Asn Arg Val Val Leu Asp Val
        500                 505                 510 acc tcc aag cca cca gga acc atc gaa tgg gag tag                      1572
Thr Ser Lys Pro Pro Gly Thr Ile Glu Trp Glu
    515                 520

<210> SEQ ID NO 6
<211> LENGTH: 523
<212> TYPE: PRT
<213> ORGANISM: Corynebacterium glutamicum

<400> SEQUENCE: 6

Val Ser Leu Gln Thr Asn His Arg Pro Val Leu Val Asp Phe Gly
1               5                   10                  15

Ala Gln Tyr Ala Gln Leu Ile Ala Arg Arg Val Arg Glu Ala Gly Ile
            20                  25                  30

Tyr Ser Glu Val Ile Pro His Thr Ala Thr Ala Asp Asp Val Arg Ala
        35                  40                  45

Lys Asn Ala Ala Ala Leu Val Leu Ser Gly Gly Pro Ser Ser Val Tyr
    50                  55                  60

Ala Glu Gly Ala Pro Ser Leu Asp Ala Glu Ile Leu Asp Leu Gly Leu
65                  70                  75                  80

Pro Val Phe Gly Ile Cys Tyr Gly Phe Gln Ala Met Thr His Ala Leu
                85                  90                  95

Gly Gly Thr Val Ala Asn Thr Gly Lys Arg Glu Tyr Gly Arg Thr Asp
            100                 105                 110

Ile Asn Val Ala Gly Gly Val Leu His Glu Gly Leu Glu Ala Cys His
        115                 120                 125

Lys Val Trp Met Ser His Gly Asp Ala Val Ser Glu Ala Pro Glu Gly
    130                 135                 140

Phe Val Val Thr Ala Ser Ser Glu Gly Ala Pro Val Ala Ala Phe Glu
145                 150                 155                 160

Asn Lys Glu Arg Lys Met Ala Gly Val Gln Tyr His Pro Glu Val Leu
                165                 170                 175
```

His Ser Pro His Gly Gln Ala Val Leu Thr Arg Phe Leu Thr Glu Ile
            180                 185                 190

Ala Gly Leu Glu Gln Asn Trp Thr Ala Ala Asn Ile Ala Glu Glu Leu
        195                 200                 205

Ile Glu Lys Val Arg Glu Gln Ile Gly Glu Asp Gly Arg Ala Ile Cys
    210                 215                 220

Gly Leu Ser Gly Gly Val Asp Ser Ala Val Ala Gly Ala Leu Val Gln
225                 230                 235                 240

Arg Ala Ile Gly Asp Arg Leu Thr Cys Val Phe Val Asp His Gly Leu
                245                 250                 255

Leu Arg Ala Gly Glu Arg Glu Gln Val Glu Lys Asp Phe Val Ala Ala
        260                 265                 270

Thr Gly Ala Lys Leu Val Thr Val Asp Glu Arg Gln Ala Phe Leu Ser
    275                 280                 285

Lys Leu Ala Gly Val Thr Glu Pro Glu Ala Lys Arg Lys Ala Ile Gly
    290                 295                 300

Ala Glu Phe Ile Arg Ser Phe Glu Arg Ala Val Ala Gly Val Leu Glu
305                 310                 315                 320

Glu Ala Pro Glu Gly Ser Thr Val Asp Phe Leu Val Gln Gly Thr Leu
                325                 330                 335

Tyr Pro Asp Val Val Glu Ser Gly Gly Ser Gly Thr Ala Asn Ile
                340                 345                 350

Lys Ser His His Asn Val Gly Gly Leu Pro Asp Asp Val Glu Phe Lys
        355                 360                 365

Leu Val Glu Pro Leu Arg Asp Leu Phe Lys Asp Glu Val Arg Ala Val
    370                 375                 380

Gly Arg Glu Leu Gly Leu Pro Glu Glu Ile Val Gly Arg Gln Pro Phe
385                 390                 395                 400

Pro Gly Pro Gly Leu Gly Ile Arg Ile Ile Gly Glu Val Thr Glu Asp
                405                 410                 415

Arg Leu Glu Thr Leu Arg His Ala Asp Leu Ile Ala Arg Thr Glu Leu
            420                 425                 430

Thr Glu Ala Gly Leu Asp Gly Val Ile Trp Gln Cys Pro Val Val Leu
    435                 440                 445

Leu Ala Asp Val Arg Ser Val Gly Val Gln Gly Asp Gly Arg Thr Tyr
450                 455                 460

Gly His Pro Ile Val Leu Arg Pro Val Ser Ser Glu Asp Ala Met Thr
465                 470                 475                 480

Ala Asp Trp Thr Arg Leu Pro Tyr Glu Val Leu Glu Lys Ile Ser Thr
                485                 490                 495

Arg Ile Thr Asn Glu Val Pro Asp Val Asn Arg Val Val Leu Asp Val
            500                 505                 510

Thr Ser Lys Pro Pro Gly Thr Ile Glu Trp Glu
    515                 520

<210> SEQ ID NO 7
<211> LENGTH: 1575
<212> TYPE: DNA
<213> ORGANISM: Corynebacterium ammoniagenes
<220> FEATURE:
<221> NAME/KEY: CDS
<222> LOCATION: (1)..(1572)

<400> SEQUENCE: 7 gtg act caa cct gca aca act ccg cgc cca gtc ctc gtg gtg gat ttc    48
Val Thr Gln Pro Ala Thr Thr Pro Arg Pro Val Leu Val Val Asp Phe

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 1   |     |     |     | 5   |     |     |     |     | 10  |     |     |     |     | 15  |     |      |
| ggt | gcc | caa | tac | gca | cag | ctg | att | gct | cgt | cgc | gta | cgt | gag | gca | tcg | 96   |
| Gly | Ala | Gln | Tyr | Ala | Gln | Leu | Ile | Ala | Arg | Arg | Val | Arg | Glu | Ala | Ser |      |
|     |     |     | 20  |     |     |     |     | 25  |     |     |     |     | 30  |     |     |      |
| att | tac | tcc | gag | gta | gtc | cca | cat | tcc | gcc | acc | gtt | aaa | gag | att | aaa | 144  |
| Ile | Tyr | Ser | Glu | Val | Val | Pro | His | Ser | Ala | Thr | Val | Lys | Glu | Ile | Lys |      |
|     |     | 35  |     |     |     |     | 40  |     |     |     |     | 45  |     |     |     |      |
| gct | aaa | aac | cct | gca | gct | ttg | att | ttg | tcc | ggt | ggc | ccg | tcc | tct | gtt | 192  |
| Ala | Lys | Asn | Pro | Ala | Ala | Leu | Ile | Leu | Ser | Gly | Gly | Pro | Ser | Ser | Val |      |
|     | 50  |     |     |     |     | 55  |     |     |     |     | 60  |     |     |     |     |      |
| tat | gcc | gat | ggc | gcc | ccg | caa | tta | aag | cct | gaa | ctg | ctc | gag | ctt | ggt | 240  |
| Tyr | Ala | Asp | Gly | Ala | Pro | Gln | Leu | Lys | Pro | Glu | Leu | Leu | Glu | Leu | Gly |      |
| 65  |     |     |     | 70  |     |     |     |     | 75  |     |     |     |     | 80  |     |      |
| gtg | cca | gtc | ttt | ggc | atc | tgc | tac | ggc | ttc | caa | gcc | atg | aac | cat | gct | 288  |
| Val | Pro | Val | Phe | Gly | Ile | Cys | Tyr | Gly | Phe | Gln | Ala | Met | Asn | His | Ala |      |
|     |     |     |     | 85  |     |     |     |     | 90  |     |     |     |     | 95  |     |      |
| ttg | ggt | ggc | aac | gtt | gcg | caa | acc | ggt | gac | cgt | gaa | tac | ggc | cgc | acc | 336  |
| Leu | Gly | Gly | Asn | Val | Ala | Gln | Thr | Gly | Asp | Arg | Glu | Tyr | Gly | Arg | Thr |      |
|     |     |     | 100 |     |     |     |     | 105 |     |     |     |     | 110 |     |     |      |
| gaa | atc | acc | cat | acc | ggt | ggt | gtg | ctg | cac | gac | ggc | tta | gaa | gaa | aac | 384  |
| Glu | Ile | Thr | His | Thr | Gly | Gly | Val | Leu | His | Asp | Gly | Leu | Glu | Glu | Asn |      |
|     |     | 115 |     |     |     |     | 120 |     |     |     |     | 125 |     |     |     |      |
| cac | aag | gtc | tgg | atg | tcc | cac | ggt | gat | gct | gtg | gat | aag | gca | cct | gag | 432  |
| His | Lys | Val | Trp | Met | Ser | His | Gly | Asp | Ala | Val | Asp | Lys | Ala | Pro | Glu |      |
|     | 130 |     |     |     |     | 135 |     |     |     |     | 140 |     |     |     |     |      |
| ggc | ttt | acc | gtg | acc | gca | tcg | tcg | gct | ggt | gcg | ccg | gtt | gca | gcg | atg | 480  |
| Gly | Phe | Thr | Val | Thr | Ala | Ser | Ser | Ala | Gly | Ala | Pro | Val | Ala | Ala | Met |      |
| 145 |     |     |     |     | 150 |     |     |     |     | 155 |     |     |     |     | 160 |      |
| gaa | tgc | gtg | gcc | aag | caa | atg | gct | ggt | gtg | caa | tac | cac | ccc | gag | gtt | 528  |
| Glu | Cys | Val | Ala | Lys | Gln | Met | Ala | Gly | Val | Gln | Tyr | His | Pro | Glu | Val |      |
|     |     |     |     | 165 |     |     |     |     | 170 |     |     |     |     | 175 |     |      |
| atg | cat | tcc | cca | cac | gga | cag | gaa | gta | ctc | gtt | cgc | ttc | ctc | acc | gag | 576  |
| Met | His | Ser | Pro | His | Gly | Gln | Glu | Val | Leu | Val | Arg | Phe | Leu | Thr | Glu |      |
|     |     |     | 180 |     |     |     |     | 185 |     |     |     |     | 190 |     |     |      |
| gta | gca | ggg | cta | gag | cag | acc | tgg | acc | tcg | gca | aat | att | gcg | cag | cag | 624  |
| Val | Ala | Gly | Leu | Glu | Gln | Thr | Trp | Thr | Ser | Ala | Asn | Ile | Ala | Gln | Gln |      |
|     |     | 195 |     |     |     |     | 200 |     |     |     |     | 205 |     |     |     |      |
| ctt | atc | gat | gat | gtc | cgc | gcg | caa | atc | ggc | cct | gaa | ggc | cgc | gct | att | 672  |
| Leu | Ile | Asp | Asp | Val | Arg | Ala | Gln | Ile | Gly | Pro | Glu | Gly | Arg | Ala | Ile |      |
|     | 210 |     |     |     |     | 215 |     |     |     |     | 220 |     |     |     |     |      |
| tgt | ggc | ctg | tcg | ggc | ggc | gtg | gac | tcc | gca | gtc | gct | gca | gcg | ctc | gtg | 720  |
| Cys | Gly | Leu | Ser | Gly | Gly | Val | Asp | Ser | Ala | Val | Ala | Ala | Ala | Leu | Val |      |
| 225 |     |     |     |     | 230 |     |     |     |     | 235 |     |     |     |     | 240 |      |
| cag | cgc | gcc | att | ggc | gac | cgt | ttg | acc | tgt | gtg | ttc | gtg | gac | cac | ggt | 768  |
| Gln | Arg | Ala | Ile | Gly | Asp | Arg | Leu | Thr | Cys | Val | Phe | Val | Asp | His | Gly |      |
|     |     |     |     | 245 |     |     |     |     | 250 |     |     |     |     | 255 |     |      |
| ctg | ctg | cgc | gcc | ggt | gag | cgt | gag | cag | gta | gaa | aag | gac | ttc | gtg | gct | 816  |
| Leu | Leu | Arg | Ala | Gly | Glu | Arg | Glu | Gln | Val | Glu | Lys | Asp | Phe | Val | Ala |      |
|     |     |     | 260 |     |     |     |     | 265 |     |     |     |     | 270 |     |     |      |
| tcg | act | ggt | gcg | aag | ctg | att | acc | gcg | cat | gaa | gct | gat | gct | ttc | ttg | 864  |
| Ser | Thr | Gly | Ala | Lys | Leu | Ile | Thr | Ala | His | Glu | Ala | Asp | Ala | Phe | Leu |      |
|     |     | 275 |     |     |     |     | 280 |     |     |     |     | 285 |     |     |     |      |
| tct | aag | ctc | gcc | ggt | gtt | acc | gat | cct | gag | gct | aag | cgc | aag | gct | atc | 912  |
| Ser | Lys | Leu | Ala | Gly | Val | Thr | Asp | Pro | Glu | Ala | Lys | Arg | Lys | Ala | Ile |      |
|     | 290 |     |     |     |     | 295 |     |     |     |     | 300 |     |     |     |     |      |
| ggc | gcg | gaa | ttc | atc | cgt | tcc | ttt | gag | cgt | gct | gtg | gca | cag | gct | ttg | 960  |
| Gly | Ala | Glu | Phe | Ile | Arg | Ser | Phe | Glu | Arg | Ala | Val | Ala | Gln | Ala | Leu |      |
| 305 |     |     |     |     | 310 |     |     |     |     | 315 |     |     |     |     | 320 |      |
| gaa | gaa | tct | cct | gaa | gac | tcc | aca | gtg | gac | ttc | ctg | gtc | cag | ggc | acc | 1008 |

```
Glu Glu Ser Pro Glu Asp Ser Thr Val Asp Phe Leu Val Gln Gly Thr
                325                 330                 335 ttg tat ccg gat gtg gtt gaa tcc ggc ggc ggt gac ggc acc gca aat      1056
Leu Tyr Pro Asp Val Val Glu Ser Gly Gly Gly Asp Gly Thr Ala Asn
        340                 345                 350 atc aag tcc cac cac aat gtt ggc ggc ctg cca gac gat gtc gaa ttc      1104
Ile Lys Ser His His Asn Val Gly Gly Leu Pro Asp Asp Val Glu Phe
                355                 360                 365 gaa ctc gtc gag cca cta cgc ctg ctt ttt aag gac gaa gtc cgt gcc      1152
Glu Leu Val Glu Pro Leu Arg Leu Leu Phe Lys Asp Glu Val Arg Ala
    370                 375                 380 gtc ggc cgc gag ctc ggc ctg cct gag gaa atc gtt gcc cgc cag cca      1200
Val Gly Arg Glu Leu Gly Leu Pro Glu Glu Ile Val Ala Arg Gln Pro
385                 390                 395                 400 ttc cct ggc cct ggc cta ggc atc cgc atc atc ggt gaa gtc acc gag      1248
Phe Pro Gly Pro Gly Leu Gly Ile Arg Ile Ile Gly Glu Val Thr Glu
                405                 410                 415 gag cgt cta gaa atc ctg cgt caa gca gac ctg att gcg cgt acc gag      1296
Glu Arg Leu Glu Ile Leu Arg Gln Ala Asp Leu Ile Ala Arg Thr Glu
        420                 425                 430 ctg acc aac gct ggc ctc gac ggt gat atc tgg cag tgc cca gtc gta      1344
Leu Thr Asn Ala Gly Leu Asp Gly Asp Ile Trp Gln Cys Pro Val Val
                435                 440                 445 ctg ctt gcc gat gtc cgc tcc gtc gga gtc caa ggc gac ggc cgc acc      1392
Leu Leu Ala Asp Val Arg Ser Val Gly Val Gln Gly Asp Gly Arg Thr
    450                 455                 460 tac ggc cac cca atc gtg ctg cgc cca gtg tca tcc gag gat gcc atg      1440
Tyr Gly His Pro Ile Val Leu Arg Pro Val Ser Ser Glu Asp Ala Met
465                 470                 475                 480 acc gcc gac tgg acc cgc gtt cct tac gac gtc cta gag aaa atc tcc      1488
Thr Ala Asp Trp Thr Arg Val Pro Tyr Asp Val Leu Glu Lys Ile Ser
                485                 490                 495 acc cgc att acc aac gaa gtc aac gac gtc aac cgc gtg gtc gtc gac      1536
Thr Arg Ile Thr Asn Glu Val Asn Asp Val Asn Arg Val Val Val Asp
        500                 505                 510 atc acc tcc aag cca ccg gga acc atc gag tgg gag taa                  1575
Ile Thr Ser Lys Pro Pro Gly Thr Ile Glu Trp Glu
                515                 520

<210> SEQ ID NO 8
<211> LENGTH: 524
<212> TYPE: PRT
<213> ORGANISM: Corynebacterium ammoniagenes

<400> SEQUENCE: 8

Val Thr Gln Pro Ala Thr Thr Pro Arg Pro Val Leu Val Val Asp Phe
1               5                   10                  15

Gly Ala Gln Tyr Ala Gln Leu Ile Ala Arg Arg Val Arg Glu Ala Ser
                20                  25                  30

Ile Tyr Ser Glu Val Val Pro His Ser Ala Thr Val Lys Glu Ile Lys
            35                  40                  45

Ala Lys Asn Pro Ala Ala Leu Ile Leu Ser Gly Gly Pro Ser Ser Val
        50                  55                  60

Tyr Ala Asp Gly Ala Pro Gln Leu Lys Pro Glu Leu Leu Glu Leu Gly
65                  70                  75                  80

Val Pro Val Phe Gly Ile Cys Tyr Gly Phe Gln Ala Met Asn His Ala
                85                  90                  95

Leu Gly Gly Asn Val Ala Gln Thr Gly Asp Arg Glu Tyr Gly Arg Thr
            100                 105                 110
```

-continued

```
Glu Ile Thr His Thr Gly Gly Val Leu His Asp Gly Leu Glu Glu Asn
        115                 120                 125

His Lys Val Trp Met Ser His Gly Asp Ala Val Asp Lys Ala Pro Glu
    130                 135                 140

Gly Phe Thr Val Thr Ala Ser Ala Gly Ala Pro Val Ala Ala Met
145                 150                 155                 160

Glu Cys Val Ala Lys Gln Met Ala Gly Val Gln Tyr His Pro Glu Val
                165                 170                 175

Met His Ser Pro His Gly Gln Glu Val Leu Val Arg Phe Leu Thr Glu
            180                 185                 190

Val Ala Gly Leu Glu Gln Thr Trp Thr Ser Ala Asn Ile Ala Gln Gln
        195                 200                 205

Leu Ile Asp Asp Val Arg Ala Gln Ile Gly Pro Glu Gly Arg Ala Ile
    210                 215                 220

Cys Gly Leu Ser Gly Gly Val Asp Ser Ala Val Ala Ala Ala Leu Val
225                 230                 235                 240

Gln Arg Ala Ile Gly Asp Arg Leu Thr Cys Val Phe Val Asp His Gly
                245                 250                 255

Leu Leu Arg Ala Gly Glu Arg Glu Gln Val Glu Lys Asp Phe Val Ala
            260                 265                 270

Ser Thr Gly Ala Lys Leu Ile Thr Ala His Glu Ala Asp Ala Phe Leu
        275                 280                 285

Ser Lys Leu Ala Gly Val Thr Asp Pro Glu Ala Lys Arg Lys Ala Ile
    290                 295                 300

Gly Ala Glu Phe Ile Arg Ser Phe Glu Arg Ala Val Ala Gln Ala Leu
305                 310                 315                 320

Glu Glu Ser Pro Glu Asp Ser Thr Val Asp Phe Leu Val Gln Gly Thr
                325                 330                 335

Leu Tyr Pro Asp Val Val Glu Ser Gly Gly Gly Asp Gly Thr Ala Asn
            340                 345                 350

Ile Lys Ser His His Asn Val Gly Gly Leu Pro Asp Asp Val Glu Phe
        355                 360                 365

Glu Leu Val Glu Pro Leu Arg Leu Leu Phe Lys Asp Glu Val Arg Ala
    370                 375                 380

Val Gly Arg Glu Leu Gly Leu Pro Glu Glu Ile Val Ala Arg Gln Pro
385                 390                 395                 400

Phe Pro Gly Pro Gly Leu Gly Ile Arg Ile Ile Gly Glu Val Thr Glu
                405                 410                 415

Glu Arg Leu Glu Ile Leu Arg Gln Ala Asp Leu Ile Ala Arg Thr Glu
            420                 425                 430

Leu Thr Asn Ala Gly Leu Asp Gly Asp Ile Trp Gln Cys Pro Val Val
        435                 440                 445

Leu Leu Ala Asp Val Arg Ser Val Gly Val Gln Gly Asp Gly Arg Thr
    450                 455                 460

Tyr Gly His Pro Ile Val Leu Arg Pro Val Ser Ser Glu Asp Ala Met
465                 470                 475                 480

Thr Ala Asp Trp Thr Arg Val Pro Tyr Asp Val Leu Glu Lys Ile Ser
                485                 490                 495

Thr Arg Ile Thr Asn Glu Val Asn Asp Val Asn Arg Val Val Val Asp
            500                 505                 510

Ile Thr Ser Lys Pro Pro Gly Thr Ile Glu Trp Glu
        515                 520
```

<210> SEQ ID NO 9
<211> LENGTH: 46
<212> TYPE: DNA
<213> ORGANISM: Artificial sequence
<220> FEATURE:
<223> OTHER INFORMATION: primer

<400> SEQUENCE: 9
aataagaatt catgacggaa acattcata agcatcgcat cctcat        46

<210> SEQ ID NO 10
<211> LENGTH: 31
<212> TYPE: DNA
<213> ORGANISM: Artificial sequence
<220> FEATURE:
<223> OTHER INFORMATION: primer

<400> SEQUENCE: 10
tgttactgca gtcaatccta taattcttga a        31

<210> SEQ ID NO 11
<211> LENGTH: 753
<212> TYPE: DNA
<213> ORGANISM: Escherichia coli
<220> FEATURE:
<221> NAME/KEY: CDS
<222> LOCATION: (1)..(750)

<400> SEQUENCE: 11

```
atg acc att aaa aat gta att tgc gat atc gac ggc gtg ctg atg cac       48
Met Thr Ile Lys Asn Val Ile Cys Asp Ile Asp Gly Val Leu Met His
1               5                   10                  15 gat aac gtc gcc gta ccg ggt gca gcg gaa ttt ttg cac ggg att atg       96
Asp Asn Val Ala Val Pro Gly Ala Ala Glu Phe Leu His Gly Ile Met
                20                  25                  30 gat aaa ggc ctg ccg ctg gtg ttg ctg acc aac tat cct tcg cag act      144
Asp Lys Gly Leu Pro Leu Val Leu Leu Thr Asn Tyr Pro Ser Gln Thr
            35                  40                  45 ggg caa gat ctg gcg aac cgc ttt gcc acc gca ggt gtc gat gta cct      192
Gly Gln Asp Leu Ala Asn Arg Phe Ala Thr Ala Gly Val Asp Val Pro
        50                  55                  60 gac agc gtg ttt tat acc tct gcg atg gcg act gcc gat ttc ctg cgt      240
Asp Ser Val Phe Tyr Thr Ser Ala Met Ala Thr Ala Asp Phe Leu Arg
65                  70                  75                  80 cgc cag gaa ggc aag aaa gcg tat gtg gtg ggc gaa ggc gca ctg att      288
Arg Gln Glu Gly Lys Lys Ala Tyr Val Val Gly Glu Gly Ala Leu Ile
                85                  90                  95 cat gaa ctg tac aaa gcc ggt ttc act att acc gat gtg aac cct gat      336
His Glu Leu Tyr Lys Ala Gly Phe Thr Ile Thr Asp Val Asn Pro Asp
                100                 105                 110 ttc gtg att gtt ggc gaa acg cgt tcc tac aac tgg gac atg atg cat      384
Phe Val Ile Val Gly Glu Thr Arg Ser Tyr Asn Trp Asp Met Met His
            115                 120                 125 aaa gca gcc tat ttc gtc gct aac ggt gca cgt ttt atc gcc acc aat      432
Lys Ala Ala Tyr Phe Val Ala Asn Gly Ala Arg Phe Ile Ala Thr Asn
        130                 135                 140 ccg gac acc cac ggg cgc ggt ttt tat ccc gct tgt ggc gcg ttg tgt      480
Pro Asp Thr His Gly Arg Gly Phe Tyr Pro Ala Cys Gly Ala Leu Cys
145                 150                 155                 160 gca ggg att gag aaa atc tcc ggg cgc aaa ccg ttc tat gtt ggt aag      528
Ala Gly Ile Glu Lys Ile Ser Gly Arg Lys Pro Phe Tyr Val Gly Lys
                165                 170                 175
```

```
ccc agc ccg tgg atc atc cgc gca gca tta aac aaa atg cag gcg cat    576
Pro Ser Pro Trp Ile Ile Arg Ala Ala Leu Asn Lys Met Gln Ala His
        180                 185                 190 tcg gaa gaa acg gtg att gtc ggc gat aac ctg cgt acc gat att ctg    624
Ser Glu Glu Thr Val Ile Val Gly Asp Asn Leu Arg Thr Asp Ile Leu
    195                 200                 205 gcc ggc ttc cag gca ggt ctg gag acg att ctg gtg ctt tct ggt gtt    672
Ala Gly Phe Gln Ala Gly Leu Glu Thr Ile Leu Val Leu Ser Gly Val
210                 215                 220 tcg tcg ctc gac gat atc gac agt atg cct ttc cgc ccc agc tgg att    720
Ser Ser Leu Asp Asp Ile Asp Ser Met Pro Phe Arg Pro Ser Trp Ile
225                 230                 235                 240 tac ccg tca gtc gct gaa atc gac gtt atc tga                        753
Tyr Pro Ser Val Ala Glu Ile Asp Val Ile
                245                 250

<210> SEQ ID NO 12
<211> LENGTH: 250
<212> TYPE: PRT
<213> ORGANISM: Escherichia coli

<400> SEQUENCE: 12

Met Thr Ile Lys Asn Val Ile Cys Asp Ile Asp Gly Val Leu Met His
1               5                   10                  15

Asp Asn Val Ala Val Pro Gly Ala Ala Glu Phe Leu His Gly Ile Met
            20                  25                  30

Asp Lys Gly Leu Pro Leu Val Leu Leu Thr Asn Tyr Pro Ser Gln Thr
        35                  40                  45

Gly Gln Asp Leu Ala Asn Arg Phe Ala Thr Ala Gly Val Asp Val Pro
    50                  55                  60

Asp Ser Val Phe Tyr Thr Ser Ala Met Ala Thr Ala Asp Phe Leu Arg
65                  70                  75                  80

Arg Gln Glu Gly Lys Lys Ala Tyr Val Gly Glu Gly Ala Leu Ile
                85                  90                  95

His Glu Leu Tyr Lys Ala Gly Phe Thr Ile Thr Asp Val Asn Pro Asp
            100                 105                 110

Phe Val Ile Val Gly Glu Thr Arg Ser Tyr Asn Trp Asp Met Met His
        115                 120                 125

Lys Ala Ala Tyr Phe Val Ala Asn Gly Ala Arg Phe Ile Ala Thr Asn
    130                 135                 140

Pro Asp Thr His Gly Arg Gly Phe Tyr Pro Ala Cys Gly Ala Leu Cys
145                 150                 155                 160

Ala Gly Ile Glu Lys Ile Ser Gly Arg Lys Pro Phe Tyr Val Gly Lys
                165                 170                 175

Pro Ser Pro Trp Ile Ile Arg Ala Ala Leu Asn Lys Met Gln Ala His
            180                 185                 190

Ser Glu Glu Thr Val Ile Val Gly Asp Asn Leu Arg Thr Asp Ile Leu
        195                 200                 205

Ala Gly Phe Gln Ala Gly Leu Glu Thr Ile Leu Val Leu Ser Gly Val
    210                 215                 220

Ser Ser Leu Asp Asp Ile Asp Ser Met Pro Phe Arg Pro Ser Trp Ile
225                 230                 235                 240

Tyr Pro Ser Val Ala Glu Ile Asp Val Ile
                245                 250

<210> SEQ ID NO 13
<211> LENGTH: 25
```

<210> SEQ ID NO 13
<211> LENGTH: 25
<212> TYPE: DNA
<213> ORGANISM: Artificial sequence
<220> FEATURE:
<223> OTHER INFORMATION: primer

<400> SEQUENCE: 13
tctgcaaagc cgcgaacaaa ggcga                                   25

<210> SEQ ID NO 14
<211> LENGTH: 25
<212> TYPE: DNA
<213> ORGANISM: Artificial sequence
<220> FEATURE:
<223> OTHER INFORMATION: primer

<400> SEQUENCE: 14
aattgctgac aaagtgcgat ttgtt                                   25

<210> SEQ ID NO 15
<211> LENGTH: 1653
<212> TYPE: DNA
<213> ORGANISM: Escherichia coli
<220> FEATURE:
<221> NAME/KEY: CDS
<222> LOCATION: (1)..(1650)

<400> SEQUENCE: 15

```
atg aaa tta ttg cag cgg ggc gtg gcg tta gcg ctg tta acc aca ttt      48
Met Lys Leu Leu Gln Arg Gly Val Ala Leu Ala Leu Leu Thr Thr Phe
1               5                   10                  15 aca ctg gcg agt gaa act gct ctg gcg tat gag cag gat aaa acc tac      96
Thr Leu Ala Ser Glu Thr Ala Leu Ala Tyr Glu Gln Asp Lys Thr Tyr
            20                  25                  30 aaa att aca gtt ctg cat acc aat gat cat cat ggg cat ttt tgg cgc     144
Lys Ile Thr Val Leu His Thr Asn Asp His His Gly His Phe Trp Arg
        35                  40                  45 aat gaa tat ggc gaa tat ggt ctg gcg gcg caa aaa acg ctg gtg gat     192
Asn Glu Tyr Gly Glu Tyr Gly Leu Ala Ala Gln Lys Thr Leu Val Asp
    50                  55                  60 ggt atc cgc aaa gag gtt gcg gct gaa ggc ggt agc gtg ctg cta ctt     240
Gly Ile Arg Lys Glu Val Ala Ala Glu Gly Gly Ser Val Leu Leu Leu
65                  70                  75                  80 tcc ggt ggc gac att aac act ggc gtg ccc gag tct gac tta cag gat     288
Ser Gly Gly Asp Ile Asn Thr Gly Val Pro Glu Ser Asp Leu Gln Asp
                85                  90                  95 gcc gaa cct gat ttt cgc ggt atg aat ctg gtg ggc tat gac gcg atg     336
Ala Glu Pro Asp Phe Arg Gly Met Asn Leu Val Gly Tyr Asp Ala Met
            100                 105                 110 gcg atc ggt aat cat gaa ttt gat aat ccg ctc acc gta tta cgc cag     384
Ala Ile Gly Asn His Glu Phe Asp Asn Pro Leu Thr Val Leu Arg Gln
        115                 120                 125 cag gaa aag tgg gcc aag ttc ccg ttg ctt tcc gcg aat atc tac cag     432
Gln Glu Lys Trp Ala Lys Phe Pro Leu Leu Ser Ala Asn Ile Tyr Gln
    130                 135                 140 aaa agt act ggc gag cgc ctg ttt aaa ccg tgg gcg ctg ttt aag cgt     480
Lys Ser Thr Gly Glu Arg Leu Phe Lys Pro Trp Ala Leu Phe Lys Arg
145                 150                 155                 160 cag gat ctg aaa att gcc gtt att ggg ctg aca acc gat gac aca gca     528
Gln Asp Leu Lys Ile Ala Val Ile Gly Leu Thr Thr Asp Asp Thr Ala
                165                 170                 175 aaa att ggt aac ccg gaa tac ttc act gat atc gaa ttt cgt aag ccc     576
Lys Ile Gly Asn Pro Glu Tyr Phe Thr Asp Ile Glu Phe Arg Lys Pro
            180                 185                 190
```

-continued

```
gcc gat gaa gcg aag ctg gtg att cag gag ctg caa cag aca gaa aag      624
Ala Asp Glu Ala Lys Leu Val Ile Gln Glu Leu Gln Gln Thr Glu Lys
        195                 200                 205 cca gac att att atc gcg gcg acc cat atg ggg cat tac gat aat ggt      672
Pro Asp Ile Ile Ile Ala Ala Thr His Met Gly His Tyr Asp Asn Gly
    210                 215                 220 gag cac ggc tct aac gca ccg ggc gat gtg gag atg gca cgc gcg ctg      720
Glu His Gly Ser Asn Ala Pro Gly Asp Val Glu Met Ala Arg Ala Leu
225                 230                 235                 240 cct gcc gga tcg ctg gcg atg atc gtc ggt ggt cac tcg caa gat ccg      768
Pro Ala Gly Ser Leu Ala Met Ile Val Gly Gly His Ser Gln Asp Pro
                245                 250                 255 gtc tgc atg gcg gca gaa aac aaa aaa cag gtc gat tac gtg ccg ggt      816
Val Cys Met Ala Ala Glu Asn Lys Lys Gln Val Asp Tyr Val Pro Gly
            260                 265                 270 acg cca tgc aaa cca gat caa caa aac ggc atc tgg att gtg cag gcg      864
Thr Pro Cys Lys Pro Asp Gln Gln Asn Gly Ile Trp Ile Val Gln Ala
        275                 280                 285 cat gag tgg ggc aaa tac gtg gga cgg gct gat ttt gag ttt cgt aat      912
His Glu Trp Gly Lys Tyr Val Gly Arg Ala Asp Phe Glu Phe Arg Asn
    290                 295                 300 ggc gaa atg aaa atg gtt aac tac cag ctg att ccg gtg aac ctg aag      960
Gly Glu Met Lys Met Val Asn Tyr Gln Leu Ile Pro Val Asn Leu Lys
305                 310                 315                 320 aag aaa gtg acc tgg gaa gac ggg aaa agc gag cgc gtg ctt tac act     1008
Lys Lys Val Thr Trp Glu Asp Gly Lys Ser Glu Arg Val Leu Tyr Thr
                325                 330                 335 cct gaa atc gct gaa aac cag caa atg atc tcg ctg tta tca ccg ttc     1056
Pro Glu Ile Ala Glu Asn Gln Gln Met Ile Ser Leu Leu Ser Pro Phe
            340                 345                 350 cag aac aaa ggc aaa gcg cag ctg gaa gtg aaa ata ggc gaa acc aat     1104
Gln Asn Lys Gly Lys Ala Gln Leu Glu Val Lys Ile Gly Glu Thr Asn
        355                 360                 365 ggt cgt ctg gaa ggc gat cgt gac aaa gtg cgt ttt gta cag acc aat     1152
Gly Arg Leu Glu Gly Asp Arg Asp Lys Val Arg Phe Val Gln Thr Asn
    370                 375                 380 atg ggg cgg ttg att ctg gca gcc caa atg gat cgc act ggt gcc gac     1200
Met Gly Arg Leu Ile Leu Ala Ala Gln Met Asp Arg Thr Gly Ala Asp
385                 390                 395                 400 ttt gcg gtg atg agc gga ggc gga att cgt gat tct atc gaa gca ggc     1248
Phe Ala Val Met Ser Gly Gly Gly Ile Arg Asp Ser Ile Glu Ala Gly
                405                 410                 415 gat atc agc tat aaa aac gtg ctg aaa gtg cag cca ttc ggc aat gtg     1296
Asp Ile Ser Tyr Lys Asn Val Leu Lys Val Gln Pro Phe Gly Asn Val
            420                 425                 430 gtg gtg tat gcc gac atg acc ggt aaa gag gtg att gat tac ctg acc     1344
Val Val Tyr Ala Asp Met Thr Gly Lys Glu Val Ile Asp Tyr Leu Thr
        435                 440                 445 gcc gtc gcg cag atg aag cca gat tca ggt gcc tac ccg caa ttt gcc     1392
Ala Val Ala Gln Met Lys Pro Asp Ser Gly Ala Tyr Pro Gln Phe Ala
    450                 455                 460 aac gtt agc ttt gtg gcg aaa gac ggc aaa ctg aac gac ctt aaa atc     1440
Asn Val Ser Phe Val Ala Lys Asp Gly Lys Leu Asn Asp Leu Lys Ile
465                 470                 475                 480 aaa ggc gaa ccg gtc gat ccg gcg aaa act tac cgt atg gcg aca tta     1488
Lys Gly Glu Pro Val Asp Pro Ala Lys Thr Tyr Arg Met Ala Thr Leu
                485                 490                 495 aac ttc aat gcc acc ggc ggt gat gga tat ccg cgc ctt gat aac aaa     1536
Asn Phe Asn Ala Thr Gly Gly Asp Gly Tyr Pro Arg Leu Asp Asn Lys
```

```
                       500                 505                 510
ccg ggc tat gtg aat acc ggc ttt att gat gcc gaa gtg ctg aaa gcg       1584
Pro Gly Tyr Val Asn Thr Gly Phe Ile Asp Ala Glu Val Leu Lys Ala
            515                 520                 525 tat atc cag aaa agc tcg ccg ctg gat gtg agt gtt tat gaa ccg aaa       1632
Tyr Ile Gln Lys Ser Ser Pro Leu Asp Val Ser Val Tyr Glu Pro Lys
    530                 535                 540 ggt gag gtg agc tgg cag taa                                           1653
Gly Glu Val Ser Trp Gln
545                 550

<210> SEQ ID NO 16
<211> LENGTH: 550
<212> TYPE: PRT
<213> ORGANISM: Escherichia coli

<400> SEQUENCE: 16

Met Lys Leu Leu Gln Arg Gly Val Ala Leu Ala Leu Leu Thr Thr Phe
1               5                   10                  15

Thr Leu Ala Ser Glu Thr Ala Leu Ala Tyr Glu Gln Asp Lys Thr Tyr
            20                  25                  30

Lys Ile Thr Val Leu His Thr Asn Asp His His Gly His Phe Trp Arg
        35                  40                  45

Asn Glu Tyr Gly Glu Tyr Gly Leu Ala Ala Gln Lys Thr Leu Val Asp
    50                  55                  60

Gly Ile Arg Lys Glu Val Ala Ala Glu Gly Gly Ser Val Leu Leu Leu
65                  70                  75                  80

Ser Gly Gly Asp Ile Asn Thr Gly Val Pro Glu Ser Asp Leu Gln Asp
                85                  90                  95

Ala Glu Pro Asp Phe Arg Gly Met Asn Leu Val Gly Tyr Asp Ala Met
            100                 105                 110

Ala Ile Gly Asn His Glu Phe Asp Asn Pro Leu Thr Val Leu Arg Gln
        115                 120                 125

Gln Glu Lys Trp Ala Lys Phe Pro Leu Leu Ser Ala Asn Ile Tyr Gln
    130                 135                 140

Lys Ser Thr Gly Glu Arg Leu Phe Lys Pro Trp Ala Leu Phe Lys Arg
145                 150                 155                 160

Gln Asp Leu Lys Ile Ala Val Ile Gly Leu Thr Thr Asp Asp Thr Ala
                165                 170                 175

Lys Ile Gly Asn Pro Glu Tyr Phe Thr Asp Ile Glu Phe Arg Lys Pro
            180                 185                 190

Ala Asp Glu Ala Lys Leu Val Ile Gln Glu Leu Gln Gln Thr Glu Lys
        195                 200                 205

Pro Asp Ile Ile Ile Ala Ala Thr His Met Gly His Tyr Asp Asn Gly
    210                 215                 220

Glu His Gly Ser Asn Ala Pro Gly Asp Val Glu Met Ala Arg Ala Leu
225                 230                 235                 240

Pro Ala Gly Ser Leu Ala Met Ile Val Gly Gly His Ser Gln Asp Pro
                245                 250                 255

Val Cys Met Ala Ala Glu Asn Lys Lys Gln Val Asp Tyr Val Pro Gly
            260                 265                 270

Thr Pro Cys Lys Pro Asp Gln Gln Asn Gly Ile Trp Ile Val Gln Ala
        275                 280                 285

His Glu Trp Gly Lys Tyr Val Gly Arg Ala Asp Phe Glu Phe Arg Asn
    290                 295                 300
```

```
Gly Glu Met Lys Met Val Asn Tyr Gln Leu Ile Pro Val Asn Leu Lys
305                 310                 315                 320

Lys Lys Val Thr Trp Glu Asp Gly Lys Ser Glu Arg Val Leu Tyr Thr
                325                 330                 335

Pro Glu Ile Ala Glu Asn Gln Gln Met Ile Ser Leu Leu Ser Pro Phe
            340                 345                 350

Gln Asn Lys Gly Lys Ala Gln Leu Glu Val Lys Ile Gly Glu Thr Asn
        355                 360                 365

Gly Arg Leu Glu Gly Asp Arg Asp Lys Val Arg Phe Val Gln Thr Asn
370                 375                 380

Met Gly Arg Leu Ile Leu Ala Ala Gln Met Asp Arg Thr Gly Ala Asp
385                 390                 395                 400

Phe Ala Val Met Ser Gly Gly Ile Arg Asp Ser Ile Glu Ala Gly
                405                 410                 415

Asp Ile Ser Tyr Lys Asn Val Leu Lys Val Gln Pro Phe Gly Asn Val
            420                 425                 430

Val Val Tyr Ala Asp Met Thr Gly Lys Glu Val Ile Asp Tyr Leu Thr
        435                 440                 445

Ala Val Ala Gln Met Lys Pro Asp Ser Gly Ala Tyr Pro Gln Phe Ala
    450                 455                 460

Asn Val Ser Phe Val Ala Lys Asp Gly Lys Leu Asn Asp Leu Lys Ile
465                 470                 475                 480

Lys Gly Glu Pro Val Asp Pro Ala Lys Thr Tyr Arg Met Ala Thr Leu
                485                 490                 495

Asn Phe Asn Ala Thr Gly Gly Asp Gly Tyr Pro Arg Leu Asp Asn Lys
            500                 505                 510

Pro Gly Tyr Val Asn Thr Gly Phe Ile Asp Ala Glu Val Leu Lys Ala
        515                 520                 525

Tyr Ile Gln Lys Ser Ser Pro Leu Asp Val Ser Val Tyr Glu Pro Lys
    530                 535                 540

Gly Glu Val Ser Trp Gln
545                 550

<210> SEQ ID NO 17
<211> LENGTH: 714
<212> TYPE: DNA
<213> ORGANISM: Escherichia coli
<220> FEATURE:
<221> NAME/KEY: CDS
<222> LOCATION: (1)..(711)

<400> SEQUENCE: 17 atg cgc aag atc aca cag gca atc agt gcc gtt tgc tta ttg ttc gct     48
Met Arg Lys Ile Thr Gln Ala Ile Ser Ala Val Cys Leu Leu Phe Ala
1               5                   10                  15 cta aac agt tcc gct gtt gcc ctg gcc tca tct cct tca ccg ctt aac     96
Leu Asn Ser Ser Ala Val Ala Leu Ala Ser Ser Pro Ser Pro Leu Asn
            20                  25                  30 cct ggg act aac gtt gcc agg ctt gct gaa cag gca ccc att cat tgg    144
Pro Gly Thr Asn Val Ala Arg Leu Ala Glu Gln Ala Pro Ile His Trp
        35                  40                  45 gtt tcg gtc gca caa att gaa aat agc ctc gca ggg cgt ccg cca atg    192
Val Ser Val Ala Gln Ile Glu Asn Ser Leu Ala Gly Arg Pro Pro Met
    50                  55                  60 gcg gtg ggg ttt gat atc gat gac acg gta ctt ttt tcc agt ccg ggc    240
Ala Val Gly Phe Asp Ile Asp Asp Thr Val Leu Phe Ser Ser Pro Gly
65                  70                  75                  80
```

```
ttc tgg cgc ggc aaa aaa acc ttc tcg cca gaa agc gaa gat tat ctg      288
Phe Trp Arg Gly Lys Lys Thr Phe Ser Pro Glu Ser Glu Asp Tyr Leu
                85                  90                  95 aaa aat cct gtg ttc tgg gaa aaa atg aac aat ggc tgg gat gaa ttc      336
Lys Asn Pro Val Phe Trp Glu Lys Met Asn Asn Gly Trp Asp Glu Phe
            100                 105                 110 agc att cca aaa gag gtc gct cgc cag ctg att gat atg cat gta cgc      384
Ser Ile Pro Lys Glu Val Ala Arg Gln Leu Ile Asp Met His Val Arg
        115                 120                 125 cgc ggt gac gcg atc ttc ttt gtg act ggt cgt agc ccg acg aaa aca      432
Arg Gly Asp Ala Ile Phe Phe Val Thr Gly Arg Ser Pro Thr Lys Thr
    130                 135                 140 gaa acg gtt tca aaa acg ctg gcg gat aat ttt cat att cct gcc acc      480
Glu Thr Val Ser Lys Thr Leu Ala Asp Asn Phe His Ile Pro Ala Thr
145                 150                 155                 160 aac atg aat ccg gtg atc ttt gcg ggc gat aaa cca ggg caa aat aca      528
Asn Met Asn Pro Val Ile Phe Ala Gly Asp Lys Pro Gly Gln Asn Thr
                165                 170                 175 aaa tcg caa tgg ctg cag gat aaa aat atc cga att ttt tat ggc gat      576
Lys Ser Gln Trp Leu Gln Asp Lys Asn Ile Arg Ile Phe Tyr Gly Asp
            180                 185                 190 tct gat aat gat att acc gcc gca cgc gat gtc ggc gct cgt ggt atc      624
Ser Asp Asn Asp Ile Thr Ala Ala Arg Asp Val Gly Ala Arg Gly Ile
        195                 200                 205 cgc att ctg cgc gcc tcc aac tct acc tac aaa ccc ttg cca caa gcg      672
Arg Ile Leu Arg Ala Ser Asn Ser Thr Tyr Lys Pro Leu Pro Gln Ala
    210                 215                 220 ggt gcg ttt ggt gaa gag gtg atc gtc aat tca gaa tac tga              714
Gly Ala Phe Gly Glu Glu Val Ile Val Asn Ser Glu Tyr
225                 230                 235

<210> SEQ ID NO 18
<211> LENGTH: 237
<212> TYPE: PRT
<213> ORGANISM: Escherichia coli

<400> SEQUENCE: 18

Met Arg Lys Ile Thr Gln Ala Ile Ser Ala Val Cys Leu Leu Phe Ala
1               5                   10                  15

Leu Asn Ser Ser Ala Val Ala Leu Ala Ser Ser Pro Ser Pro Leu Asn
            20                  25                  30

Pro Gly Thr Asn Val Ala Arg Leu Ala Glu Gln Ala Pro Ile His Trp
        35                  40                  45

Val Ser Val Ala Gln Ile Glu Asn Ser Leu Ala Gly Arg Pro Pro Met
    50                  55                  60

Ala Val Gly Phe Asp Ile Asp Asp Thr Val Leu Phe Ser Ser Pro Gly
65                  70                  75                  80

Phe Trp Arg Gly Lys Lys Thr Phe Ser Pro Glu Ser Glu Asp Tyr Leu
                85                  90                  95

Lys Asn Pro Val Phe Trp Glu Lys Met Asn Asn Gly Trp Asp Glu Phe
            100                 105                 110

Ser Ile Pro Lys Glu Val Ala Arg Gln Leu Ile Asp Met His Val Arg
        115                 120                 125

Arg Gly Asp Ala Ile Phe Phe Val Thr Gly Arg Ser Pro Thr Lys Thr
    130                 135                 140

Glu Thr Val Ser Lys Thr Leu Ala Asp Asn Phe His Ile Pro Ala Thr
145                 150                 155                 160

Asn Met Asn Pro Val Ile Phe Ala Gly Asp Lys Pro Gly Gln Asn Thr
```

```
              165                 170                 175
Lys Ser Gln Trp Leu Gln Asp Lys Asn Ile Arg Ile Phe Tyr Gly Asp
        180                 185                 190

Ser Asp Asn Asp Ile Thr Ala Ala Arg Asp Val Gly Ala Arg Gly Ile
        195                 200                 205

Arg Ile Leu Arg Ala Ser Asn Ser Thr Tyr Lys Pro Leu Pro Gln Ala
    210                 215                 220

Gly Ala Phe Gly Glu Glu Val Ile Val Asn Ser Glu Tyr
225                 230                 235

<210> SEQ ID NO 19
<211> LENGTH: 54
<212> TYPE: DNA
<213> ORGANISM: Artificial sequence
<220> FEATURE:
<223> OTHER INFORMATION: primer1 for disrupting nagD

<400> SEQUENCE: 19
tgggtagtcc atgaccatta aaaatgtaat ttgcgacgct caagttagta taaa       54

<210> SEQ ID NO 20
<211> LENGTH: 54
<212> TYPE: DNA
<213> ORGANISM: Artificial sequence
<220> FEATURE:
<223> OTHER INFORMATION: primer2 for disrupting nagD

<400> SEQUENCE: 20
aacgtcgatt tcagcgactg acgggtaaat ccagcttgaa gcctgctttt ttat       54

<210> SEQ ID NO 21
<211> LENGTH: 54
<212> TYPE: DNA
<213> ORGANISM: Artificial sequence
<220> FEATURE:
<223> OTHER INFORMATION: primer1 for disrupting ushA

<400> SEQUENCE: 21
ggagagaagt atgaaattat tgcagcgggg cgtggccgct caagttagta taaa       54

<210> SEQ ID NO 22
<211> LENGTH: 54
<212> TYPE: DNA
<213> ORGANISM: Artificial sequence
<220> FEATURE:
<223> OTHER INFORMATION: primer2 for disrupting ushA

<400> SEQUENCE: 22
ccagctcacc tcacctttcg gttcataaac actcactgaa gcctgctttt ttat       54

<210> SEQ ID NO 23
<211> LENGTH: 54
<212> TYPE: DNA
<213> ORGANISM: Artificial sequence
<220> FEATURE:
<223> OTHER INFORMATION: primer1 for disrupting aphA

<400> SEQUENCE: 23
agggaaaaat atgcgcaaga tcacacaggc aatcagcgct caagttagta taaa       54

<210> SEQ ID NO 24
<211> LENGTH: 54
<212> TYPE: DNA
<213> ORGANISM: Artificial sequence
```

-continued

```
<220> FEATURE:
<223> OTHER INFORMATION: primer2 for disrupting aphA

<400> SEQUENCE: 24
ttctgaattg acgatcacct cttcaccaaa cgcacctgaa gcctgctttt ttat        54
```

METHOD FOR PRODUCING 5'-GUANYLIC ACID

This application claims priority under 35 U.S.C. §119 to Japanese Patent Application No. 2009-185920, filed on Aug. 10, 2009, which is incorporated in its entirety by reference. The Sequence Listing in electronic format filed herewith is also hereby incorporated by reference in its entirety (File Name: 2010-08-06T_US-439_Seq_List; File Size: 72 KB; Date Created: Aug. 6, 2010).

BACKGROUND OF THE INVENTION

1. Field of the Invention

The present invention relates to a method for producing 5'-guanylic acid, and a novel microorganism used for this production. 5'-guanylic acid is useful as a food seasoning, a pharmaceutical, and in raw materials thereof.

2. Brief Description of the Related Art

Known examples of industrial methods for producing 5'-guanylic acid, also known as guanosine-5'-monophosphate, or "GMP", include producing guanosine by fermentation and then subjecting it to enzymatic phosphorylation, to obtain 5'-guanylic acid (JP 07-231793 A, JP 10-201481 A, WO 96/37603 and JP 2001-245676 A).

Other methods of producing GMP have been reported, including culturing both an *Escherichia* bacterium with increased GMP synthetase activity, and a *Brevibacterium ammoniagenes* which is able to biosynthesize large amounts of adenosine-triphosphate (ATP) (hereinafter also referred to as the "regeneration of ATP") and synthesize GMP from 5'-xanthylic acid (XVIP) in a culture medium containing XIVIP, and ammonia or glutamine. ATP is necessary for glucose metabolism, and XIVIP can be converted into GMP with high efficiency. In this way, GMP can be produced and accumulated in the culture (Tatsuro Fujio, et al., Biosci. Biotech. Biochem., 1997, 61(5), pp. 840-845.).

Methods to produce GMP by fermentation have also been proposed. For example, in JP 56-12438 B, a method for producing GMP is disclosed wherein a mutant strain of the genus *Bacillus* with adenine auxotrophy, resistance to decoyinine or methionine sulfoxide, and the ability to produce GMP is cultured, and GMP is produced and recovered from the culture medium. Furthermore, JP 2002-355087 A discloses a method for producing GMP using a strain produced by deleting two kinds of 5'-nucleotidase genes in an *Escherichia* bacterium having an ability to produce inosinic acid (inosinic acid-5'-monophosphate, hereinafter also referred to as "IMP") and amplifying the IMP dehydrogenase and GMP synthetase genes. This strain is cultured, and GMP produced and recovered from the culture medium. However, in general, the yield of GMP is not sufficient in direct fermentation and therefore such methods are not practical as compared to the above-described enzyme methods.

As mentioned above, research has been conducted relating to the production of 5'-guanylic acid, and several successful examples have been reported. However, the function of the nucleotidase(s) is/are not fully understood. Several nucleotidases have been found and it is known that when deleted, the yield of 5'-guanylic acid is improved (JP 2002-355087 A and WO 2006/078132). However, it is difficult to completely inhibit degradation of the product, which can be problematic.

SUMMARY OF THE INVENTION

An aspect of the present invention is to create a novel microorganism which can be used in a method for producing GMP from XMP, and which is capable of converting XMP into GMP with high efficiency.

It is described herein that, by using a microorganism of the genus *Escherichia* modified so that the nagD gene does not function normally and GMP synthetase activity is increased, XMP is converted into GMP with high efficiency.

It is one aspect of the present invention to provide a method for producing 5'-guanylic acid, comprising reacting a microorganism with xanthylic acid to produce 5'-guanylic acid, and collecting 5'-guanylic acid, wherein said microorganism is able to convert xanthylic acid into 5'-guanylic acid and has been modified so that a nagD gene does not function normally, and 5'-guanylic acid synthetase activity is enhanced.

It is another aspect of the present invention to provide the method as described above, wherein 5'-guanylic acid synthetase activity is enhanced by increasing expression of a guaA gene in said microorganism.

It is another aspect of the present invention to provide the method as described above, wherein said the guaA gene encodes a protein selected from the group consisting (A) and (B):

(A) a protein comprising the amino acid sequence of SEQ ID NO:2;

(B) a protein comprising the amino acid sequence of SEQ ID NO:2, but which includes substitution, deletion, insertion, or addition of one or several amino acids, and the protein has 5'-guanylic acid synthetase activity.

It is another aspect of the present invention to provide the method as described above, wherein said microorganism has been further modified so that a gene selected from the group consisting of ushA, aphA, and combinations thereof do/does not function normally.

It is another aspect of the present invention to provide the method as described above, wherein said microorganism is bacteria selected from the group consisting of bacteria belonging to Enterobacteriaceae family, *Bacillus* bacteria and coryneform bacteria.

It is another aspect of the present invention to provide the method as described above, wherein said microorganism belongs to the genus *Escherichia*.

It is another aspect of the present invention to provide the method as described above, wherein said microorganism is *Escherichia coli*.

It is another aspect of the present invention to provide a microorganism which is able to convert xanthylic acid into 5'-guanylic acid, wherein said microorganism has been modified so that 5'-guanylic acid synthetase activity is enhanced by increasing expression of guaA gene and that nagD gene does not function normally, wherein said microorganism does not have increased expression of a guaB gene.

It is another aspect of the present invention to provide the microorganism as described above, wherein said microorganism has been further modified so that a gene selected from the group consisting of ushA, aphA, and combinations thereof do/does not function normally.

It is another aspect of the present invention to provide the microorganism as described above, wherein said microorganism is bacteria selected from the group consisting of bacteria belonging to Enterobacteriaceae family, *Bacillus* bacteria and coryneform bacteria.

It is another aspect of the present invention to provide the microorganism as described above, wherein said microorganism belongs to the genus *Escherichia*.

It is another aspect of the present invention to provide the microorganism as described above, wherein said microorganism is *Escherichia coli*.

BRIEF DESCRIPTION OF THE DRAWINGS

FIG. 1 (B) is a graph showing changes in the concentrations of XMP and GMP upon reacting the JM109ΔnagD/pSTV29-Ptac-guaA strain with XMP.

FIG. 2 (B) is a graph showing changes in the concentrations of XMP and GMP upon reacting the JM109ΔushAΔnagD/pSTV29-Ptac-guaA strain with XMP.

FIG. 3 (B) is a graph showing changes in the concentrations of XMP and GMP upon reacting the JM109ΔushAΔaphAΔnagD/pSTV29-Ptac-guaA strain with XMP.

DESCRIPTION OF THE PREFERRED EMBODIMENTS

Figure 1:
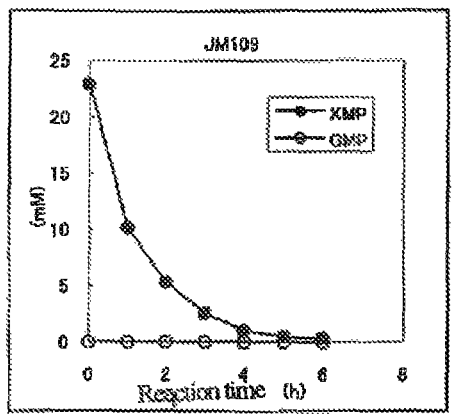
FIG. 1 (A) is a graph showing changes in the concentrations of XMP and GMP upon reacting the JM109/pSTV29-Ptac-guaA strain with XMP.
Figure 1:
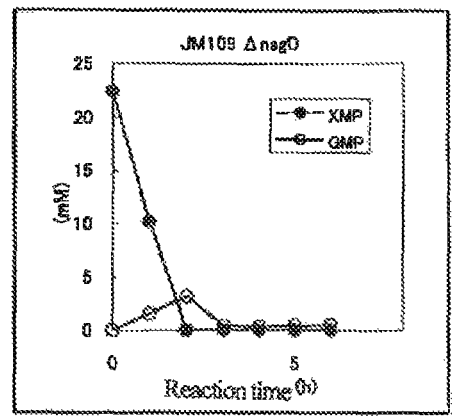

The present invention will now be described in detail.

<I> Microorganism

A microorganism in accordance with the presently disclosed subject matter can be modified so that, first, the nagD gene does not function normally, and second, GMP synthetase activity is increased. The microorganism is able to convert XMP into GMP.

Examples of the microorganism include bacteria belonging to Enterobacteriaceae family, coryneform bacteria, and bacteria belonging to the genus *Bacillus*.

Examples of the bacteria belonging to Enterobacteriaceae family include bacteria belonging to the following genus of bacteria: *Escherichia, Pantoea, Enterobacter, Klebsiella, Serratia, Erwinia, Salmonella*, and *Morganella*. The bacteria belonging to the genus *Escherichia* are not restricted as long as they belong to the genus *Escherichia*, and particular examples include the bacteria described by Neidhardt et al. (Neidhardt, F R. C. et al., *Escherichia coli* and *Salmonella typhimurium*, American Society for Microbiology, Washington D.C., 1208, table 1), such as *Escherichia coli*. Examples of the bacteria belonging to the genus *Enterobacter* include *Enterobacter agglomerans* and *Enterobacter aerogenes*, and examples of the bacteria belonging to the genus *Pantoea* include *Pantoea ananatis*.

Examples of the coryneform bacteria include bacteria classified into coryneform bacteria according to the classification known to those skilled in the art of microbiology, bacteria which had been classified into the genus *Brevibacterium* but was reclassified into the genus *Corynebacterium* (Int. J. Syst. Bacteriol., 41, 255 (1991)), and bacteria belonging to the genus *Brevibacterium* which is related to the genus *Corynebacterium*. The followings are examples of such coryneform bacteria.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes*
*Corynebacterium herculis*
*Brevibacterium divaricatum*
*Brevibacterium flavum*
*Brevibacterium immariophilum*
*Brevibacterium lactofermentum*
*Brevibacterium roseum*
*Brevibacterium saccharolyticum*
*Brevibacterium thiogenitalis*
*Corynebacterium ammoniagenes*
*Brevibacterium album*
*Brevibacterium cerinum*
*Microbacterium ammoniaphilum*

As the bacteria belonging to the genus *Bacillus*, bacteria classified into the genus *Bacillus* according to the classification known to those skilled in the art of microbiology are included, and particular examples include, but are not limited to, *Bacillus subtilis* and *Bacillus amyloliquefaciens*.

Methods to enhance GMP synthetase activity in the above-described microorganisms will now be described.

The phrase "modified so that GMP synthetase activity is enhanced" means that GMP synthetase activity is higher than that of an unmodified strain, for example, a wild-type strain, of a microorganism such as a bacterium belonging to the genus *Escherichia*.

GMP synthetase is an enzyme (EC 6.3.4.1) which catalyzes the following reaction, and the term "GMP synthetase activity" means the activity to catalyze the reaction to produce GMP from XIVIP.

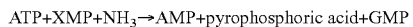

$$ATP + XMP + NH_3 \rightarrow AMP + \text{pyrophosphoric acid} + GMP$$

The GMP synthetase activity can be measured by, for example, determination of the rate of reduction of NADH by the method described in Spector (Spector, T., Methods Enzymol., 1978, 51, p. 219).

In order to enhance GMP synthetase activity, the expression level of the guaA gene can be increased. Examples of methods to increase the expression level include increasing the copy number of a DNA encoding GMP synthetase in the cells of a microorganism. The copy number can be increased by linking a DNA fragment encoding GMP synthetase to a vector which functions in the chosen microorganism to prepare a recombinant DNA, followed by transformation of the microorganism with the DNA. As a result of the increase in the copy number of the gene encoding GMP synthetase (guaA gene) in the cell of the transformant, GMP synthetase activity increases.

The copy number in the cells can also be increased by placement of a large number of the GMP synthetase gene on the chromosomal DNA of the above-described host. The GMP synthetase gene can be placed onto the chromosomal DNA of a bacterium such as an *Escherichia* bacterium in a high copy number by homologous recombination using, as targets, sequences present on the chromosome in a high copy number. Examples of such sequences include repetitive DNAs and inverted repeats present at the ends of transposable elements. Alternatively, as disclosed in JP 2-109985 A, it is also possible to place a gene on a transposon and allow the transposon to transpose. By any of these methods, the copy number of the GMP synthetase gene in the transformant increases, and as a result, the GMP synthetase activity increases.

Examples of vectors which can be used to introduce the above gene include plasmid vectors such as pSTV29, pMW218, and pUC19; and phage vectors such as λ1059, λBF101, and M13 mp9. Transposons such as Mu, Tn10, and Tn5 can also be used.

Since the nucleotide sequence of the DNA encoding GMP synthetase is known, the gene can be obtained by synthesizing primers based on the sequence, and amplifying it by PCR using the chromosomal DNA of a microorganism such as a bacterium belonging to the genus *Escherichia* as the template. Examples of the guaA gene of *Escherichia coli* include the nucleotide sequence of SEQ ID NO:1. By preparing a probe based on the nucleotide sequence of this gene and by hybridization, a desired DNA fragment can be selected from the chromosomal DNA library of a bacterium belonging to the genus *Escherichia*. Alternatively, a DNA fragment encoding GMP synthetase may be chemically synthesized based on the known nucleotide sequence. For example, the guaA gene of *Escherichia coli* can be cloned using primers having the sequences of SEQ ID NOs: 9 and 10.

Furthermore, a gene encoding a protein with a similar function to GMP synthetase can be obtained from other microorganisms based on the above-described nucleotide sequence.

Examples of the GMP synthetase gene (guaA) of *Bacillus subtilis* include the nucleotide sequence of SEQ ID NO: 3. The amino acid sequence encoded by this nucleotide sequence is shown in SEQ ID NO: 4. Examples of the GMP synthetase gene (guaA) of *Corynebacterium glutamicum* include the nucleotide sequence of SEQ ID NO: 5. The amino acid sequence encoded by this nucleotide sequence is shown in SEQ ID NO: 6.

Examples of the GMP synthetase gene (guaA) of *Corynebacterium ammoniagenes* include the nucleotide sequence of SEQ ID NO: 7. The amino acid sequence encoded by this nucleotide sequence is shown in SEQ ID NO: 8.

As described above, since various nucleotide sequences of the guaA gene may be different depending on the genus, species and/or strain of the origin microorganism, the guaA gene may be a variant of the above-described genes.

The protein encoded by the guaA gene can have a sequence identity of not less than 80%, or in another example less than 90%, or in another example not less than 95%, or in another example not less than 98% to the entire amino acid sequence of SEQ ID NO: 2, 4, 6 or 8 as long as it has the GMP synthetase activity. The identity between amino acid sequences and between nucleotide sequences can be determined using, for example, BLAST, an algorithm by Karlin and Altschul (Pro. Natl. Acad. Sci. USA, 90, 5873 (1993)), or FASTA by Pearson (Methods Enzymol., 183, 63 (1990)). Based on the algorithm BLAST, programs called BLASTN and BLASTX have been developed.

The guaA gene is not limited to the wild-type gene, and can include mutants or an artificially modified gene encoding a protein having the amino acid sequence of SEQ ID NOs: 2, 4, 6 or 8, but which includes substitution, deletion, insertion, addition or inversion of one or several amino acids, as long as the function of the encoded protein, that is, the GMP synthetase activity is not impaired. The meaning of the expression "one or several" varies depending on the positions and/or types of the amino acid residues in the spatial structure of the protein, but in particular, can mean 1 to 20, or in another example 1 to 10, or in another example 1 to 5. The substitution can be a conservative substitution, and the expression "conservative substitution" can mean mutual substitution among Phe, Trp and Tyr when the substitution site has an aromatic amino acid, among Leu, Ire and Val when the substitution site has a hydrophobic amino acid, between Gln and Asn when the substitution site has a polar amino acid, among Lys, Arg and His when the substitution site has a basic amino acid, between Asp and Glu when the substitution site has an acidic amino acid, and between Ser and Thr when the substitution site has an amino acid having a hydroxyl group. Examples of a conservative substitution include the substitution of Ala by Ser or Thr, substitution of Arg by Gln, His or Lys, substitution of Asn by Glu, Gln, Lys, His or Asp, substitution of Asp by Asn, Glu or Gln, substitution of Cys by Ser or Ala, substitution of Gln by Asn, Glu, Lys, His, Asp or Arg, substitution of Glu by Gly, Asn, Gln, Lys or Asp, substitution of Gly by Pro, substitution of His by Asn, Lys, Gln, Arg or Tyr, substitution of Ire by Leu, Met, Val or Phe, substitution of Leu by Ile, Met, Val or Phe, substitution of Lys by Asn, Glu, Gln, His or Arg, substitution of Met by Ile, Leu, Val or Phe, substitution of Phe by Trp, Tyr, Met, Ile or Leu, substitution of Ser by Thr or Ala, substitution of Thr by Ser or Ala, substitution of Trp by Phe or Tyr, substitution of Tyr by His, Phe or Trp, and substitution of Val by Met, Ile or Leu. Examples of a substitution, deletion, insertion, addition, inversion or the like of amino acids as described above can also include naturally occurring mutations (mutants and variants), such as ones based on individual differences and species differences among microorganisms having the guaA gene.

Furthermore, the guaA gene may be a DNA capable of hybridizing under stringent conditions with the complement of the nucleotide sequence of SEQ ID NO: 1, 3, 5 or 7, or with a probe which can be prepared from the sequence, which DNA encodes a protein having the GMP synthetase activity. The term "stringent conditions" can mean conditions in which so-called specific hybrids are formed but nonspecific hybrids are not formed. Although it is difficult to clearly express these conditions with numerical values, for example, they are conditions wherein DNAs having a high identity hybridize with each other, such as those having an identity of 80%, or in another example not less than 90%, or in another example not less than 95%, or in another example not less than 98%, but DNAs having an identity less than the above-mentioned percentage do not hybridize to each other. Stringent conditions can also include when washing is carried out once, or in another example 2 or 3 times at a salt concentration equivalent to 1×SSC and 0.1% SDS at 60° C. which are normal washing conditions for Southern hybridization, or in another example 0.1×SSC and 0.1% SDS at 60° C., or in another example 0.1×SSC and 0.1% SDS at 68° C.

The above descriptions about the variants of the gene are also similarly applicable to the later-mentioned nagD gene, ushA gene, aphA gene, and other genes.

DNA can be introduced into a microorganism by the method of C. T. Chung (C. T. Chung et al., Proc. Natl. Acad. Sci. USA, 86, 2172-2175 (1989)), the method of D. M. Morrison (Methods in Enzymology, 68, 326 (1979)), the method of increasing the permeability to DNA by treatment of a recipient bacterial cell with calcium chloride (Mandel, M. and Higa, A., J. Mol. Biol., 53, 159 (1970)), or the like.

Besides amplification of the gene as described above, the expression level of the GMP synthetase gene can also be enhanced by replacing an expression regulatory sequence such as a promoter of the GMP synthetase gene on the chromosomal DNA or on a plasmid with a stronger expression regulatory sequence. For example, the lac promoter, trp promoter, trc promoter, and tac promoter are known to be strong promoters. Furthermore, as disclosed in WO 00/18935, it is also possible to introduce several nucleotide substitutions in the promoter region of the gene to alter the promoter to a stronger one. By such promoter replacement or alteration, expression of the GMP synthetase gene can be enhanced, and therefore GMP synthetase activity increases.

The increase in the expression level of the guaA gene can be detected by Northern blotting, RT-PCR method, or the like.

The method for modifying the microorganism as described above so that nagD gene does not function normally will now be described.

The phrase "modified so that nagD gene does not function normally" can mean a decrease in or elimination of the activity of the protein encoded by the nagD gene, a decrease in or elimination of transcription of the gene, or a decrease in the translation efficiency of the gene.

The nagD gene in *E. coli* exists as a part of the nagBACD operon, which is involved in assimilation of N-acetylglucosamine. It is known that expression of this nagBACD operon gene is induced by the addition to the culture medium of N-acetylglucosamine, which is a type of sugar constituting a major component of the cell walls of bacteria (Plumbridge J A., Mol. Micobiol. (1989) 3. 505-515). The NagD protein encoded by nagD in *E. coli* is known to belong to the haloacid dehalogenase (HAD) family based on its conservative structural characteristics and based on in vivo experiments. The NagD protein has nucleotidase activity on GMP and 5'-uridylic acid (uridine-5'-monophosphate; also referred to as "UMP") (Tremblay L W., Biochemistry, (2006) 45. 1183-1193). However, since 23 types of HAD family proteins exist on the genome of *E. coli* and they show a very wide range of substrate specificities (Kuznetsova et al., J. Biol. Chem., (2006) 281., 36149-36161), the physiological roles of the NagD protein in the cell have not been reported.

Modification of nagD gene so that it does not function normally can be achieved by the following methods. For example, the nagD gene can be replaced on the chromosome with a nagD gene which does not function normally, which can be referred to as a "disrupted-type nagD gene", by homologous recombination using genetic recombination (Experiments in Molecular Genetics, Cold Spring Harbor Laboratory press (1972); Matsuyama, S, and Mizushima, S., J. Bacteriol., 162, 1196 (1985)).

In homologous recombination, introduction into bacterial cells of a plasmid or the like having a sequence homologous to a sequence on the chromosome causes recombination at the position of the sequence having the homology at a certain frequency, leading to incorporation of the entire plasmid into the chromosome. If this is followed by further recombination at the position in the homologous sequence on the chromosome, the plasmid is eliminated again, but at this time, depending on the position at which the recombination occurs, the disrupted gene may be fixed on the chromosome and the original normal gene may be removed together with the plasmid from the chromosome. By selecting such strains, a strain in which the normal nagD gene on the chromosome has been replaced with the disrupted-type nagD gene can be obtained.

Examples of the method for such gene substitution using homologous recombination include the method (see WO 2005/010175) called "Red-driven integration" (Proc. Natl. Acad. Sci. USA, 2000, vol. 97, No. 12, pp. 6640-6645). In this method, a linear DNA is combined with an excision system derived from phage (J. Bacteriol. 2002 September; 184(18): 5200-3). Methods using a plasmid having a temperature sensitive replication origin are also included (Proc. Natl. Acad. Sci. USA, 2000, vol. 97, No. 12, pp. 6640-6645; U.S. Pat. No. 6,303,383 B; and JP 05-007491 A).

Site-directed mutagenesis by gene substitution using homologous recombination as described above can also be carried out by using a plasmid which is not able to replicate in the chosen host. Furthermore, the nagD can also be disrupted by using a plasmid containing the nagD gene into which a marker gene such as a drug resistance gene is inserted. The plasmid is incapable of replicating in the chosen microorganism. That is, the transformant which was obtained by transformation with the plasmid and shows the drug-resistance phenotype has the marker gene incorporated in the chromosomal DNA. Since this marker gene is highly likely to be incorporated by homologous recombination into the nagD gene sequence and the nagD gene on the chromosome, the gene-disrupted strains can be efficiently selected.

In particular, the disrupted-type nagD gene can be obtained by causing one or more nucleotide substitutions, deletions, insertions, additions and/or inversions in the nucleotide sequence(s) of the coding region, promoter region, and/or the like by deletion of a certain region(s) the gene by restriction enzyme digestion and ligation, insertion of other DNA fragments (marker gene or the like) into the gene, site-directed mutagenesis (Kramer, W. and Frits, H. J., Methods in Enzymology, 154, 350 (1987)), and/or treatment by chemical drugs such as sodium hypochlorite, hydroxylamine and/or the like (Shortie, D. and Nathans, D., Proc., Natl., Acad., Sci., U.S.A., 75, 270 (1978)). As a result, the activity of NagD protein and/or transcription of the nagD gene can be decreased or eliminated.

The sequence of nagD gene has been reported, and the gene can be easily obtained by PCR, hybridization or the like based on the reported sequence. Examples of the nagD gene from *E. coli* include a DNA encoding the amino acid sequence of SEQ ID NO: 12. The nagD gene can be obtained, for example, from the chromosomal DNA of *Escherichia coli* by PCR using the primers of SEQ ID NOs: 13 and 14.

The nagD genes from other microorganisms can also be obtained based on their known sequences or their sequence homologies with the above-described nagD gene of *E. coli*, and can also be used to modify the microorganisms.

The nagD gene can have a sequence identity sufficient to cause homologous recombination with the nagD gene on the chromosome of the chosen microorganism, and for example, it can encode an amino acid sequence having an identity of not less than 70%, or in another example not less than 80%, or in another example not less than 90%, or in another example not less than 95%, to the entire amino acid sequence of SEQ ID NO: 12.

Disruption of the gene of interest can be confirmed by analyzing the gene on the chromosome by Southern blotting or PCR.

A mutant strain in which an active NagD protein is not produced can also be obtained by treating the chosen microorganism with ultraviolet radiation or a mutating agent such as N-methyl-N'-nitrosoguanidine (NTG) or nitrous acid.

The bacterium can be further modified so that the ushA gene and/or aphA gene do/does not function normally. Such a mutant strain or recombinant strain can be obtained by modifying these genes so that the activities of the 5'-nucleotidases encoded by the genes are decreased or eliminated, or transcription of the genes are decreased or eliminated. Such a mutant strain or recombinant strain can be obtained in the same manner as in the above-described mutant strain or recombinant strain in which the nagD gene does not function normally.

The sequence of the ushA gene has been reported, and it can be easily obtained by PCR, hybridization or the like based on the reported sequence. Examples of the ushA gene of *E. coli* include the DNA encoding the amino acid sequence of SEQ ID NO: 16.

The ushA genes from other microorganisms can also be obtained based on their known sequences or their sequence homologies with the above-described ushA gene of *E. coli*, and used to modify the chosen microorganism.

The ushA gene can have a sequence identity sufficient to cause homologous recombination with the ushA gene on the chromosome of the chosen microorganism, and for example, it can encode an amino acid sequence having an identity of not less than 70%, or in another example not less than 80%, or in another example not less than 90%, or in another example not less than 95% to the entire amino acid sequence of SEQ ID NO: 16.

The sequence of the aphA gene has been reported, and it can be easily obtained by PCR, hybridization or the like based on the reported sequence. Examples of the aphA gene of *E. coli* include a DNA encoding the amino acid sequence of SEQ ID NO: 18.

The aphA genes from other microorganisms can also be obtained based on their known sequences or their sequence homologies with the above-described aphA gene of *E. coli*, and used to modify the chosen microorganism.

The aphA gene can have a sequence identity sufficient to cause homologous recombination with the aphA gene on the chromosome of the chosen microorganism, and for example, it can encode an amino acid sequence having an identity of not less than 70%, or in another example not less than 80%, or in another example not less than 90%, or in another example not less than 95% to the entire amino acid sequence of SEQ ID NO: 18.

A microorganism is described which is able to convert xanthylic acid into 5'-guanylic acid. The microorganism can be modified so that GMP synthetase activity is enhanced by increasing expression of the guaA gene and so that nagD gene does not function normally. The microorganism also does not have increased expression of the guaB gene. This microorganism can also be modified so that ushA gene and/or aphA gene do/does not function normally.

<II> Method for Production of GMP

GMP can be obtained by reacting the above-described microorganism, which has been modified so that the nagD gene does not function normally and GMP synthetase activity is increased, with XIVIP to convert XIVIP into GMP.

In the culture of the microorganism, any carbon source can be used as long as the chosen microorganism can assimilate it, and examples include carbohydrates such as glucose, fructose, sucrose, molasses, blackstrap molasses and starch hydrolysates; alcohols such as ethanol, glycerin and sorbitol; organic acids such as pyruvic acid, lactic acid and acetic acid; amino acids such as glycine, alanine, glutamic acid and aspartic acid. Examples of the nitrogen source which can be used include ammonia; various inorganic and organic ammonium salts such as ammonium chloride, ammonium sulfate, ammonium nitrate, ammonium carbonate, ammonium acetate and ammonium phosphate; urea; various amino acids; peptones; NZ amine; meat extracts; yeast extracts; corn steep liquor; casein hydrolysates; and fish meals and digests thereof. Examples of the inorganic substance which can be used include primary potassium phosphate, secondary potassium phosphate, magnesium sulfate, magnesium phosphate, sodium chloride, ferrous sulfate, manganese sulfate, zinc sulfate and calcium carbonate. When the chosen microorganism requires specific nutrients such as amino acids, nucleic acids and/or vitamins for its growth, appropriate amounts of these substances can be added to the culture medium.

The culture can be carried out under appropriate conditions, such as a pH between 5.0 and 8.5, and a temperature between 15° C. to 45° C., under aerobic conditions for about 5 hours to 72 hours. To adjust the pH, an inorganic, organic, acidic, or alkaline substance, or ammonia gas or the like can be used.

Conversion of XIVIP into GMP can be carried out by direct inoculation of the product of the culture, inoculation of only the microbial cells after centrifugation, or inoculation of a suspension of the microbial cells in an appropriate solution, into the reaction solution containing XIVIP. The concentration of the substrate XIVIP is not restricted as long as it is sufficient for producing a collectable amount of GMP, and can be in the range of 1 to 200 mM.

In the method for producing GMP, the microbial cells in the culture can be processed and then used after being processed. Examples of the types of processing include fixation of the cells with acrylamide, carrageenan or the like.

The carbon source, nitrogen source, and inorganic substances which are present in the conversion reaction solution can be the same carbon source, nitrogen source and inorganic substances as described above for culturing the microorganism. When the chosen microorganism requires specific nutrients such as amino acids, nucleic acids, and/or vitamins for its growth, appropriate amounts of these substances are added to the reaction solution.

An organic solvent can be added to the reaction solution to activate the cell permeability of nucleotides. Examples of the organic solvent include xylene, toluene, benzene, fatty acid alcohols, and ethyl acetate, at a concentration of between 0.1 to 30 ml/L. The reaction can be carried out under appropriate conditions, such as a pH of 5.0 to 8.5, and a temperature between 15° C. to 45° C., under aerobic or anaerobic conditions for about 1 hour to 7 days. To adjust the pH, an inorganic or organic substance, acidic or alkaline substance, ammonia gas, or the like can be used. Chemically synthesized XMP, commercially available XMP, XIVIP produced by fermentation, or the like can be used.

Collection of GMP from the reaction solution can be carried out by a combination of known methods, such as ion-exchange and precipitation.

EXAMPLES

The present invention will now be described in more detail by referring to the following non-limiting Examples.

Example 1

<1-1> Construction of a nagD Gene-Disrupted Strain Derived from the JM109 Strain The parent strain *Escherichia coli* JM109 is often used as a host for DNA cloning. First, JM109 was used to construct a strain in which the NagD protein was unable to be produced. The NagD protein is encoded by the nagD gene (GenBank Accession No. X14135; SEQ ID NO: 11).

Deletion of the nagD gene was carried out by a method called "Red-driven integration", which was first developed by Datsenko and Wanner (Proc. Natl. Acad. Sci. USA, 2000, vol. 97, No. 12, pp. 6640-6645), using an excision system derived from λ phage (J. Bacteriol. 2002 September; 184(18): 5200-3. Interactions between integrase and excisionase in the phage lambda excisive nucleoprotein complex. Cho E H, Gumport R I, Gardner J F). Using the Red-driven integration method, a gene-disrupted strain can be constructed in one step using a PCR product obtained using synthetic oligonucleotide primers which were designed such that they have parts of the gene of interest in their 5' regions and parts of an antibiotic resistance gene in their 3' regions. By further combining the excision system derived from λ phage with the above method, the antibiotic resistance gene incorporated into the gene-disrupted strain can be eliminated.

The plasmid pMW118-attL-Cm-attR was used as the template for PCR. The plasmid pMW118-attL-Cm-attR (WO2006078039) is produced by insertion of the attL and attR genes, which are attachment sites for λ phage, and the cat gene, which is an antibiotic resistance gene, into pMW118 (manufactured by TAKARA BIO INC.) in the order of attL-cat-attR.

PCR was carried out using the synthetic oligonucleotide primers of SEQ ID NOs: 19 and 20. Each of these primers has a sequence which corresponds to the end of attL or attR in the 3' end and to a part of the nagD gene, which is the gene of interest, in the 5' end.

The amplified PCR product was purified using an agarose gel, and the purified PCR product was introduced to the Escherichia coli JM109 strain, which contains the plasmid pKD46 which has a temperature-sensitive replication origin, by electroporation. The plasmid pKD46 (Proc. Natl. Acad. Sci. USA, 2000, vol. 97, No. 12, p 6640-6645) contains a DNA fragment of 2154 nucleotides (GenBank/EMBL Accession No. J02459; 31088th to 33241st) of λ phage, which includes the genes encoding Red recombinase (γ, β and exo genes) for the λRed homologous recombination system. This system is controlled by the arabinose-inducible $P_{araB}$ promoter. The plasmid pKD46 is necessary for incorporation of the PCR product into the chromosome of the JM109 strain.

The competent cells for electroporation were prepared as follows. That is, the Escherichia coli JM109 strain cultured in LB medium containing 100 mg/L ampicillin at 30° C. overnight was diluted 100-fold in 5 mL of SOB medium (Molecular cloning: A Laboratory Manual, 2nd ed., Sambrook, J. et al., Cold Spring Harbor Laboratory Press (1989)) containing ampicillin (20 mg/L) and L-arabinose (1 mM). The diluted cells were allowed to grow at 30° C. under aeration until the $OD_{600}$ reaches 0.6, and concentrated 100-fold, followed by washing 3 times with 10% glycerol, and prepared for electroporation. The electroporation was carried out using 70 μl of the competent cells and about 100 ng of the PCR product. After the electroporation, 1 mL of SOC medium (Molecular Cloning: A Laboratory Manual, 2nd ed., Sambrook, J. et al., Cold Spring Harbor Laboratory Press (1989)) was added to the cells, and the cells were cultured at 37° C. for 2.5 hours, followed by a plate culture on L-agar medium containing Cm (Chloramphenicol) (25 mg/L) at 37° C., and selection of Cm-resistant recombinant cells. Then, to eliminate the pKD46 plasmid, the cells were passaged 2 times on L-agar medium containing Cm at 42° C., and the ampicillin resistance of the colonies was assayed, to obtain an ampicillin-sensitive strain lacking pKD46.

Deletion of the nagD gene in the mutant strain was confirmed by PCR. The nagD-deficient strain was named JM109ΔnagD::att-cat.

Subsequently, to eliminate the att-cat genes introduced into the nagD gene, the above-described pMW-intxis-ts was used as a helper plasmid. pMW-intxis-ts carries a gene encoding integrase (Int) and a gene encoding excisionase (Xis) of λ phage, and has a temperature-sensitive replication origin. When pMW-intxis-ts is introduced, it recognizes attL or attR on the chromosome and causes recombination to excise the gene between attL and attR, and as a result, only the attL or attR sequence remains on the chromosome.

Competent cells of the JM109ΔnagD::att-cat strain obtained as described above were prepared according to a conventional method and transformed with the helper plasmid pMW-intxis-ts, followed by a plate culture at 30° C. on L-agar medium containing 50 mg/L ampicillin, and followed by selection of an ampicillin-resistant strain.

To eliminate the pMW-intxis-ts plasmid, cells were passaged on L-agar medium at 42° C., and ampicillin resistance and chloramphenicol resistance of the resulting colonies were assayed, to obtain a chloramphenicol-and-ampicillin-sensitive strain in which the nagD gene is disrupted, and lacking att-cat and pMW-intxis-ts. This strain was named JM109ΔnagD.

<1-2> Construction of the GMP Synthetase Expression Plasmid pSTV29-Ptac-guaA and Introduction of the Plasmid into the JM109 Strain and the JM109ΔnagD Strain The GMP synthetase expression plasmid pSTV29-Ptac-guaA was constructed as follows. The guaA gene of Escherichia coli was amplified by PCR using the primers of SEQ ID NO: 9 and SEQ ID NO: 10. The amplified fragment was purified, and the restriction sites at both ends were digested with EcoRI and PstI. The digested fragment was linked to pKK223-3 (GenBank Accession No. M77749), which had been similarly digested with EcoRI and PstI, and the plasmid pKK223-guaA in which the guaA gene is incorporated immediately downstream of the tac promoter was selected. This plasmid was digested with BamHI and HindIII so that it contains the tac promoter. The digested fragment was linked to pSTV29 which had been similarly digested with BamHI and HindIII, and the plasmid pSTV29-Ptac-guaA in which the guaA gene is incorporated immediately downstream of the tac promoter was selected. This was introduced into the JM109 strain and the above-described JM109ΔnagD strain to obtain the JM109/pSTV29-Ptac-guaA and JM109ΔnagD/pSTV29-Ptac-guaA strains, respectively.

<1-3> Conversion of XMP into GMP Using the JM109/pSTV29-Ptac-guaA and JM109ΔnagD/pSTV29-Ptac-guaA Strains The conversion reaction from XMP to GMP was evaluated in the above strains. The following describes the method for preparing the bacterial cells, the reaction method, the composition of the reaction solution, and the method of analysis for the evaluation of the conversion reaction from XIVIP to GMP.

Method for Preparing Bacterial Cells:

The JM109/pSTV29-Ptac-guaA and the JM109ΔnagD/pSTV29-Ptac-guaA strains were evenly applied onto LB medium plates, followed by culturing at 37° C. overnight. On the following day, an amount of bacterial cells equivalent to 1/32 of the total amount of the cells on the plate were inoculated in 500-ml Sakaguchi flasks each containing 120 ml of LB medium, and cultured at 37° C. overnight. After centrifuging, 600 ml of the culture LB medium and the obtained bacterial cells were used for 60 ml of the reaction solution.

Method of Reaction:

The cultured bacterial cells corresponding to 600 ml of the above-mentioned LB medium were recovered with a medicine spoon and inoculated to 60 ml of the later-mentioned reaction solution to start the reaction. The reaction was carried out at 42° C. while adding aqueous ammonia to maintain a pH of 7.2.

Composition of Reaction Solution:

| | |
|---|---|
| 25 mM | XMP |
| 50 g/L | Glucose |
| 9.2 g/L | Sodium hexametaphosphate |
| 5 g/L | $MgSO_4 \cdot 7H_2O$ |
| 10 g/L | $KH_2PO_4$ |
| 3 ml/L | Xylene |

Method of Analysis:

Over time, 500 μl of the reaction solution was sampled, and the reaction was stopped by dilution with KOH. The stopped reaction solution was filtered and 10 μl of the solution was subjected to HPLC analysis. The conditions for the analysis were as follows.

Column: Asahipak GS-220HQ (7.6 mm diameter, 30 cm)
Eluent: 0.2 M $NaH_2PO_4$ (pH 3.98)
Temperature: 55° C.
How rate: 0.6 ml/minute
Detection: Ultraviolet (254 nm) absorbance The results are shown in FIG. 1. The JM109/pSTV29-Ptac-guaA strain produced GMP, but GMP did not accumulate because of a high degradation activity (GMP <0.06 g/L). Alternatively, the JM109ΔnagD/pSTV29-Ptac-guaA strain accumulated in the reaction solution about 1.7 g/L of GMP at a maximum of 2 hours after the start of the reaction.

Example 2

<2-1> Construction of an ushA Gene-Disrupted Strains Derived from the JM109 and JM109ΔnagD Strains The JM109 and JM109ΔnagD strains obtained in <1-1> in Example 1 were used to construct a strain unable to produce UshA. UshA is encoded by the ushA gene (GenBank Accession No. X03895; SEQ ID NO: 14). In the same manner as in the above-described method for disruption of the nagD gene, the ushA gene was disrupted using the primers of SEQ ID NOs: 21 and 22 as the primers. Thereby, the JM109ΔushA and JM109ΔushAΔnagD strains were obtained.

<2-2> Introduction of the GMP Synthetase Expression Plasmid pSTV29-Ptac-guaA into the JM109ΔushA and JM109ΔushAΔnagD Strains The GMP synthetase expression plasmid pSTV29-Ptac-guaA described in Example 1 was introduced to the JM109ΔushA and JM109ΔushAΔnagD strains to obtain the JM109ΔushA/pSTV29-Ptac-guaA and JM109ΔushAΔnagD/pSTV29-Ptac-guaA strains, respectively.

<2-3> Conversion of XMP into GMP Using the JM109ΔushA/pSTV29-Ptac-guaA and JM109ΔushAΔnagD/pSTV29-Ptac-guaA Strains The conversion reaction from XMP to GMP was evaluated for the above strains. The evaluation was carried out in the same manner as in <1-3> in Example 1.

Figure 2:
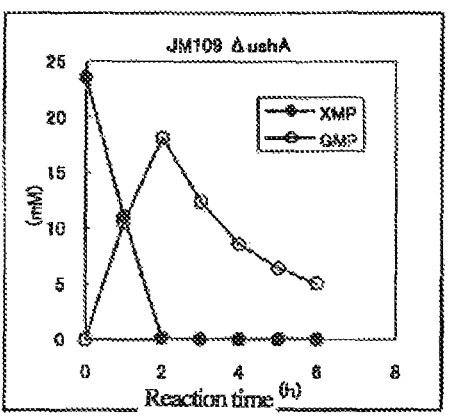
FIG. 2 (A) is a graph showing changes in the concentrations of XMP and GMP upon reacting the JM109ΔushA/pSTV29-Ptac-guaA strain with XMP.
Figure 2:
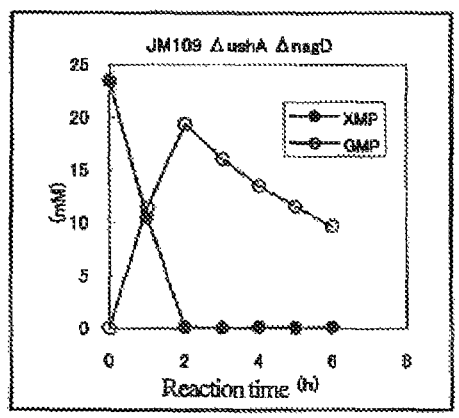

The results are shown in FIG. 2. It was shown that the JM109ΔushA/pSTV29-Ptac-guaA strain accumulated about 9.7 g/L of GMP at a maximum of 2 hours after the start of the reaction, and the JM109ΔushAΔnagD/pSTV29-Ptac-guaA strain accumulated in the reaction solution about 10.3 g/L of GMP at a maximum of 2 hours after the start of the reaction.

Example 3

<3-1> Construction of the aphA Gene-Disrupted Strains Derived from the JM109ΔushA and the JM109ΔushAΔnagD Strains The JM109ΔushA and the JM109ΔushAΔnagD strains obtained in <2-1> in Example 2 were used to construct a strain unable to produce AphA. AphA is encoded by the aphA gene (GenBank Accession No. X86971; SEQ ID NO: 17). In the same manner as in the above described method for disruption of the nagD gene, the aphA gene was disrupted using the primers of SEQ ID NOs: 23 and 24 as the primers. Thereby, the JM109ΔushAΔaphA and JM109ΔushAΔaphAΔnagD strains were obtained.

<3-2> Introduction of the GMP Synthetase Expression Plasmid pSTV29-Ptac-guaA into the JM109ΔushAΔaphA and JM109ΔushAΔaphAΔnagD Strains The GMP synthetase expression plasmid pSTV29-Ptac-guaA described in Example 1 was introduced to the JM109ΔushAΔaphA and the JM109ΔushAΔaphAΔnagD strains to obtain the JM109ΔushAΔaphA/pSTV29-Ptac-guaA and the JM109ΔushAΔaphAΔnagD/pSTV29-Ptac-guaA strains, respectively.

<3-3> Conversion of XMP into GMP Using the JM109ΔushAΔaphA/pSTV29-Ptac-guaA and JM109ΔushAΔaphAΔnagD/pSTV29-Ptac-guaA Strains The conversion reaction from XMP to GMP was evaluated in the above strains. The evaluation was carried out in the same manner as in <1-3> in Example 1, except that the XMP concentration in the reaction solution was 50 mM.

Figure 3:
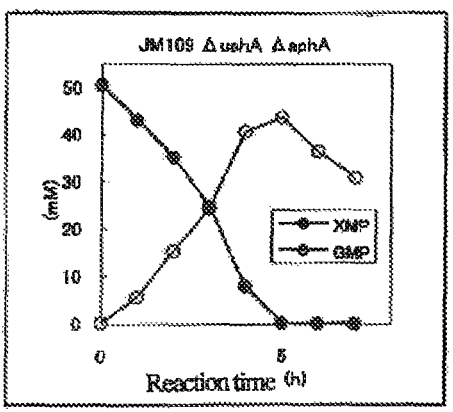
FIG. 3 (A) is a graph showing changes in the concentrations of XMP and GMP upon reacting the JM109ΔushAΔaphA/pSTV29-Ptac-guaA strain with XMP.
Figure 3:
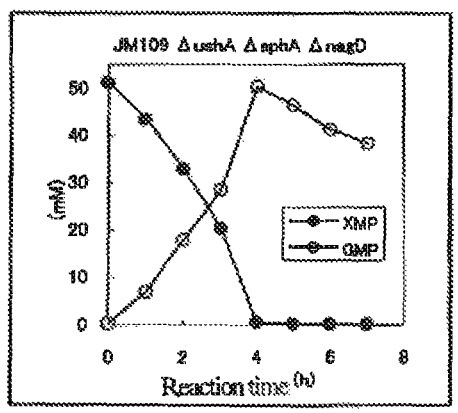

The results are shown in FIG. 3. It was shown that the JM109ΔushAΔaphA/pSTV29-Ptac-guaA strain accumulated about 23.3 g/L of GMP at a maximum of 5 hours after the start of the reaction, and the JM109ΔushAΔaphAΔnagD/pSTV29-Ptac-guaA strain accumulated in the reaction solution about 26.9 g/L of GMP at a maximum of 4 hours after the start of the reaction.

Example 4

<4-1> Construction of the aphA Gene-Disrupted Strains Derived from the JM109 and JM109ΔnagD Strains The JM109 and the JM109ΔnagD strains obtained in <1-1> in Example 1 were used to construct strains which were unable to produce AphA. As shown in Example 3, the aphA gene was disrupted using the primers of SEQ ID NOs: 23 and 24 as the primers. Thereby, the JM109ΔaphA and JM109ΔaphAΔnagD strains were obtained.

<4-2> Introduction of the GMP Synthetase Expression Plasmid pSTV29-Ptac-guaA to the JM109ΔaphA and JM109ΔaphAΔnagD Strains The GMP synthetase expression plasmid pSTV29-Ptac-guaA described in Example 1 was introduced into the JM109ΔaphA and the JM109ΔaphAΔnagD strains to obtain the JM109ΔaphA/pSTV29-Ptac-guaA and JM109ΔaphAΔnagD/pSTV29-Ptac-guaA strains, respectively.

As in Examples 1 to 3, conversion of XIVIP into GMP can be evaluated for these strains, and increases in the accumulated amounts of GMP can be confirmed.

INDUSTRIAL APPLICABILITY

According to the present invention, GMP, which is useful as a food seasoning and a pharmaceutical and raw materials thereof, can be efficiently produced.

DESCRIPTIONS FOR SEQUENCE LISTING

SEQ ID NO:1 Nucleotide sequence of *E. coli* GMP synthetase (GMPS) gene (guaA)
SEQ ID NO:2 Amino acid sequence of *E. coli* GMPS
SEQ ID NO:3 Nucleotide sequence of *B. subtilis* GMPS gene (guaA)
SEQ ID NO:4 Amino acid sequence of *B. subtilis* GMPS
SEQ ID NO:5 Nucleotide sequence of *C. glutamicum* GMPS gene (guaA)
SEQ ID NO:6 Amino acid sequence of *C. glutamicum* GMPS
SEQ ID NO:7 Nucleotide sequence of *C. ammoniagenes* GMPS gene (guaA)
SEQ ID NO:8 Amino acid sequence of *C. ammoniagenes* GMPS
SEQ ID NO:9 Nucleotide sequence of a primer for cloning *E. coli* guaA gene
SEQ ID NO:10 Nucleotide sequence of a primer for cloning *E. coli* guaA gene
SEQ ID NO:11 Nucleotide sequence of *E. coli* nagD gene
SEQ ID NO:12 Amino acid sequence of *E. coli* NagD
SEQ ID NO:13 Nucleotide sequence of a primer for cloning *E. coli* nagD gene
SEQ ID NO:14 Nucleotide sequence of a primer for cloning *E. coli* nagD gene
SEQ ID NO:15 Nucleotide sequence of *E. coli* ushA gene
SEQ ID NO:16 Amino acid sequence of *E. coli* UshA
SEQ ID NO:17 Nucleotide sequence of *E. coli* aphA gene
SEQ ID NO:18 Amino acid sequence of *E. coli* AphA
SEQ ID NO:19 Nucleotide sequence of a primer for disruption of *E. coli* nagD gene
SEQ ID NO:20 Nucleotide sequence of a primer for disruption of *E. coli* nagD gene
SEQ ID NO:21 Nucleotide sequence of a primer for disruption of *E. coli* ushA gene
SEQ ID NO:22 Nucleotide sequence of a primer for disruption of *E. coli* ushA gene
SEQ ID NO:23 Nucleotide sequence of a primer for disruption of *E. coli* aphA gene
SEQ ID NO:24 Nucleotide sequence of a primer for disruption of *E. coli* aphA gene

The invention claimed is:

1. A method for producing 5'-guanylic acid comprising:
A) reacting a microorganism with xanthylic acid to produce 5'-guanylic acid, and
B) collecting 5'-guanylic acid;
wherein said microorganism is able to convert xanthylic acid into 5'-guanylic acid, and has been modified so that:
a) a nagD gene does not function normally, and
b) 5'-guanylic acid synthetase activity is enhanced as compared to a non-modified microorganism by increasing expression of a guaA gene in said microorganism,
wherein said guaA gene encodes a protein comprising an amino acid sequence having an identity of not less than 95% to the entire amino acid sequence of SEQ ID NO: 2, 4, 6, or 8, and
wherein said protein has 5'-guanylic acid synthetase activity, and wherein said microorganism is bacteria selected from the group consisting of Enterobacteriaceae bacteria, *Bacillus* bacteria, and coryneform bacteria.

2. The method according to claim 1, wherein said guaA gene encodes a protein selected from the group consisting of:
(A) a protein comprising the amino acid sequence of SEQ ID NO:2, 4, 6, or 8; and
(B) a protein comprising the amino acid sequence of SEQ ID NO:2, 4, 6, or 8 but which includes substitution, deletion, insertion, or addition of one to 10 amino acids, and the protein has 5'-guanylic acid synthetase activity.

3. The method according to claim 1, wherein said microorganism has been further modified so that a gene selected from the group consisting of ushA, aphA, and combinations thereof do/does not function normally.

4. The method according to claim 1, wherein said microorganism belongs to the genus *Escherichia*.

5. The method according to claim 4, wherein said microorganism is *Escherichia coli*.

6. A microorganism which is able to convert xanthylic acid into 5'-guanylic acid, wherein said microorganism has been modified so that:
a) 5'-guanylic acid synthetase activity is enhanced as compared to a non-modified microorganism by increasing expression of a guaA gene, and
b) a nagD gene does not function normally,
wherein said microorganism does not have increased expression of a guaB gene,
wherein said guaA gene encodes a protein comprising an amino acid sequence having an identity of not less than 95% to the entire amino acid sequence of SEQ ID NO: 2, 4, 6, or 8, and wherein said protein has 5'-guanylic acid synthetase activity, and
wherein said microorganism is bacteria selected from the group consisting of Enterobacteriaceae bacteria, *Bacillus* bacteria, and coryneform bacteria.

7. The microorganism according to claim 6, wherein said microorganism has been further modified so that a gene selected from the group consisting of ushA, aphA, and combinations thereof do/does not function normally.

8. The microorganism according to claim 6, wherein said microorganism belongs to the genus *Escherichia*.

9. The microorganism according to claim 8, wherein said microorganism is *Escherichia coli*.

10. The method according to claim 1, wherein said nagD gene is disrupted.

11. The method according to claim 1, wherein said nagD gene encodes a protein comprising an amino acid sequence having an identity of not less than 95% to the entire amino acid sequence of SEQ ID NO: 12.

12. The microorganism according to claim 6, wherein said nagD gene is disrupted.

13. The microorganism according to claim 6, wherein said nagD gene encodes a protein comprising an amino acid sequence having an identity of not less than 95% to the entire amino acid sequence of SEQ ID NO: 12.

14. The method according to claim 3, wherein said microorganism has been further modified so that a gene selected from the group consisting of ushA, aphA, and combinations thereof is/are disrupted.

15. The microorganism according to claim 7, wherein said microorganism has been further modified so that a gene selected from the group consisting of ushA, aphA, and combinations thereof is/are disrupted.

* * * * *